US011174317B2

(12) United States Patent
Kunugi et al.

(10) Patent No.: US 11,174,317 B2
(45) Date of Patent: Nov. 16, 2021

(54) THERAPEUTIC AGENT FOR MENTAL ILLNESS COMPRISING IL-6 INHIBITOR AS ACTIVE INGREDIENT

(71) Applicants: NATIONAL CENTER OF NEUROLOGY AND PSYCHIATRY, Tokyo (JP); CHUGAI SEIYAKU KABUSHIKI KAISHA, Tokyo (JP)

(72) Inventors: Hiroshi Kunugi, Tokyo (JP); Chisato Wakabayashi, Tokyo (JP)

(73) Assignees: National Center of Neurology and Psychiatry, Tokyo (JP); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/579,309

(22) PCT Filed: Jun. 3, 2016

(86) PCT No.: PCT/JP2016/066638
§ 371 (c)(1),
(2) Date: Dec. 4, 2017

(87) PCT Pub. No.: WO2016/195088
PCT Pub. Date: Dec. 8, 2016

(65) Prior Publication Data
US 2018/0186887 A1 Jul. 5, 2018

(30) Foreign Application Priority Data
Jun. 4, 2015 (JP) .............................. JP2015-113800

(51) Int. Cl.
C07K 16/28 (2006.01)
A61K 39/395 (2006.01)
A61K 45/00 (2006.01)
A61P 25/18 (2006.01)
A61K 39/00 (2006.01)

(52) U.S. Cl.
CPC ........ C07K 16/2866 (2013.01); A61K 39/395 (2013.01); A61K 45/00 (2013.01); A61P 25/18 (2018.01); A61K 2039/505 (2013.01); C07K 2317/24 (2013.01)

(58) Field of Classification Search
CPC combination set(s) only.
See application file for complete search history.

(56) References Cited

U.S. PATENT DOCUMENTS

| 8,440,196 B1 | 5/2013 | Funakoshi et al. |
| 2004/0071706 A1 | 4/2004 | Ito et al. |
| 2004/0115197 A1 | 6/2004 | Yoshizaki et al. |
| 2006/0134113 A1 | 6/2006 | Mihara |
| 2007/0036785 A1 | 2/2007 | Kishimoto et al. |
| 2010/0048587 A1 | 2/2010 | Cook et al. |
| 2012/0201804 A1 | 8/2012 | Williams et al. |
| 2013/0202588 A1 | 8/2013 | Nishimura |
| 2015/0031709 A1 | 1/2015 | Campbell et al. |

FOREIGN PATENT DOCUMENTS

| EP | 0628639 A1 | 12/1994 |
| EP | 0783893 A1 | 7/1997 |
| EP | 2305306 A1 | 4/2011 |
| JP | 2009120501 A | 6/2009 |
| JP | P2012524112 A | 10/2012 |
| JP | P2014221815 A | 11/2014 |
| JP | P2015510513 A | 4/2015 |
| WO | WO-1992019759 A1 | 11/1992 |
| WO | WO-1996011020 A1 | 4/1996 |
| WO | WO-1996012503 A1 | 5/1996 |
| WO | WO-1998042377 A1 | 10/1998 |
| WO | WO-1999047170 A1 | 9/1999 |
| WO | WO-2000010607 A1 | 3/2000 |
| WO | WO-2002003492 A1 | 1/2002 |
| WO | WO-2002080969 A1 | 10/2002 |
| WO | WO-2004/039826 | 5/2004 |
| WO | WO-2007/143168 | 12/2007 |
| WO | WO-2008/045140 | 4/2008 |
| WO | WO-2008/144753 | 11/2008 |
| WO | WO-2008/144757 | 11/2008 |
| WO | WO-2008/144763 | 11/2008 |
| WO | WO-2009052454 A2 | 4/2009 |
| WO | WO-2009148148 A1 | 12/2009 |
| WO | W0-2010/065078 | 6/2010 |
| WO | WO-2010/065072 | 6/2010 |
| WO | WO-2010/065077 | 6/2010 |
| WO | WO-2010/065079 | 6/2010 |
| WO | WO-2011/066369 | 6/2011 |
| WO | WO-2011/066374 | 6/2011 |
| WO | WO-2011149051 A1 | 12/2011 |
| WO | WO-2013119895 A1 | 8/2013 |

OTHER PUBLICATIONS

Hirano, T., et al., "Complementary DNA for a novel human interleukin (BSF-2) that induces B lymphocytes to produce immunoglobulin," Nature 324:73-76, Macmillian Publishers Limited (1986).
Akira, S., et al., "Interleukin-6 in Biology and Medicine," Adv. in Immunology 54:1-78, Elsevier Inc. (1993).
Lotz, M., et al., "B Cell Stimulating Factor 2/Interleukin 6 is a Costimulant for Human Thymocytes and T Lymphocytes," J. Exp. Med. 167:1253-1258, The Rockefeller University Press (1988).
Taga, T., et al., "Receptors for B Cell Stimulatory Factor 2—Quantitation, Specificity, Distribution, and Regulation of Their Expression," J. Exp. Med. 166:967-981, The Rockefeller University Press (1987).
Yamasaki, K., et al., "Cloning and Expression of the Human Interleukin-6 (BSF-2/IFNβ 2) Receptor," Science 12; 241(4867):825-828 (1988).
Taga, T., et al., "Interleukin-6 Triggers the Association of Its Receptor with a Possible Signal Transducer, gp130," Cell 58(3):573-581, Elsevier Inc. (1989).

(Continued)

Primary Examiner — Olga N Chernyshev
(74) Attorney, Agent, or Firm — Nixon & Vanderhye P.C.

(57) ABSTRACT

The present invention provides a novel therapeutic agent for mental illness. The therapeutic agent for mental illness comprises an IL-6 inhibitor as an active ingredient.

4 Claims, 9 Drawing Sheets

(56) References Cited

OTHER PUBLICATIONS

Sasayama, D., et al., "Association of plasma IL-6 and soluble IL-6 receptor levels with the Asp358Ala polymorphism of the IL-6 receptor gene in schizophrenic patients," J. Psychiatr. Res. 45(11):1439-1444, Elsevier Ltd. (2011).

Sasayama, D., et al., "ITIH3 polymorphism may confer susceptibility to psychiatric disorders by altering the expression levels of GLT8D1," J. Psychiatr. Res. 50:79-83, Elsevier Inc. (2014).

Potvin, S., et al., "Inflammatory Cytokine Alterations in Schizophrenia: A Systemic Quantitative Review," Biol. Psychiatry 63(8):801-808, Elsevier Inc. (2008).

Noto, C., et al., "Effects of Risperidone on Cytokine Profile in Drug-Naïve First-Episode Psychosis," Int. J. Neuropsychopharmacol. 18(4):1-8 (2015).

Smith, S. E. P., et al., "Maternal Immune Activation Alters Fetal Brain Development through Interleukin-6," J. Neurosci. 27(40):10695-10702 (2007).

Cano, P., et al., "Effect of a High-fat Diet on 24-Hour Pattern of Circulating Adipocytokines in Rats," Obesity 17(10):1866-1871 (2009).

Labouesse, M. A., et al., "Chronic high fat diet consumption impairs sensorimotor gating in mice," Psychoneuroendocrinology 38:2562-2574 (2013).

Kohl, S., et al., "Prepulse inhibition in psychiatric disorders—Apart from schizophrenia," J. Psychiatr. Res. 47(4):445-452, Elsevier Inc. (2013).

Braff, D. L., et al., "Human studies of prepulse inhibition of startle: normal subjects, patient groups, and pharmacological studies," Psychopharmacology 156:234-258 (2001).

Miller, B. J., "An Open-label Trial of Adjunctive Tocilizumab in Schizophrenia," Biol. Psychiatry 75(9), Supplement 29S, Abstract No. 87 (May 2014).

International Search Report for International Application No. PCT/JP2016/066638, Japanese Patent Office, Tokyo, dated Jul. 12, 2016.

Lipina, T. V., et al., "Maternal Immune Activation during Gestation Interacts with Disc1 Point Mutation to Exacerbate Schizophrenia-Related Behaviors in Mice," J. Neuroscience 33(18):7654-7666 (2013).

Extended European Search Report dated Dec. 17, 2018 in European Patent Application No. EP16803519.4.

Clinicaltrials.gov, NCT02034474, Tocilizumab as Add-On Treatment For Residual Positive, Negative, and Cognitive Symptoms of Schizophrenia, Feb. 25, 2015.

Clinicaltrials.gov, Archive History for NCT01696929, An Open-Label Trial of Tocilizumab in Schizophrenia, Nov. 4, 2014.

Clinicaltrials.gov, Archive History for NCT02034474, Dec. 3, 2015.

Clinicaltrials.gov, Archive History for NCT01696929, An Open-Label Trial of Tocilizumab in Schizophrenia, Sep. 3, 2015.

Brietzke et al., Medical Hypotheses, vol. 76, No. 1, 2011, pp. 21-23.

Behrens et al., Journal of Neuroscience, vol. 28, No. 51, 2008, pp. 13957-13966.

Miller et al., The Journal of Clinical Psychiatry, vol. 77, No. 2, 2016, pp. 275-276.

Zhang et al., Translational Psychiatry, vol. 7, No. 5, 2017, p. e1138.

Giebel, L. B., et al., "Screening of Cyclic Peptide Phage Libraries Identifies Ligands That Bind Streptavidin with High Affinities," Biochem., 34:15430-15435 (1995).

Bloch, M. H., et al., "A systematic review: antipsychotic augmentation with treatment refractory obsessive-compulsive disorder," Molecular Psychiatry, 11:622-632 (2006).

Eddy, C. M., et al., "Treatment strategies forties in Tourette syndrome," Ther Adv Neurol Disord., 4(1):25-45 (2011).

HALDOL® Label, Reference ID: 2870332, Ortho-McNeil-Janssen Pharmaceuticals, Inc., 2010.

Huys, D., et al., "Update on the role of antipsychotics in the treatment of Tourette syndrome," Neuropsychiatric Disease and Treatment, 8:95-104 (2012).

prepulse 84 dB; F(2,69)= 3.81, p = 0.027, prepulse 90 dB; F(2,69)= 5.07, p= 0.009.
One-way ANOVA followed by Bonferroni's *post hoc* analysis,
*$p < 0.05$ (ND + vehicle vs. HFD + vehicle), # $p < 0.05$ (HFD +vehicle vs. HFD + MR16-1)

☐ ND + vehicle
▨ HFD + vehicle
■ HFD + MR16-1

☐ ND + vehicle
▨ HFD + vehicle
■ HFD + MR16-1

THERAPEUTIC AGENT FOR MENTAL ILLNESS COMPRISING IL-6 INHIBITOR AS ACTIVE INGREDIENT

CROSS-REFERENCE TO RELATED APPLICATIONS

This application is a U.S. National Phase of PCT Application No. PCT/JP2016/066638, filed Jun. 3, 2016, which claims the benefit of Japanese Patent Application No. 2015-113800, filed Jun. 4, 2015, each of which is incorporated herein by reference.

TECHNICAL FIELD

The present invention relates to a therapeutic agent for mental illness. More specifically, the present invention relates to a therapeutic agent for mental illness comprising an interleukin 6 (IL-6) inhibitor as an active ingredient.

BACKGROUND ART

Interleukin 6 (IL-6) is a cytokine also called B cell stimulatory factor 2 (BSF2) or interferon β2. IL-6 has been discovered as a differentiation factor involved in the activation of cells of B lymphocytic series (Non Patent Literature 1) and then found to be a multifunctional cytokine that influences the functions of various cells (Non Patent Literature 2). IL-6 has been reported to induce the maturation of cells of T lymphocytic series (Non Patent Literature 3).

IL-6 transduces its biological activity via two proteins on cells. One of them is an IL-6 receptor which is a ligand-binding protein with a molecular weight of approximately 80 kD to which IL-6 binds (Non Patent Literatures 4 and 5). The IL-6 receptor exists in a membrane-bound form that is expressed on a cell membrane in a transmembrane manner, and also exists as a soluble IL-6 receptor consisting mainly of its extracellular region.

The other is a non-ligand-binding membrane protein gp130 with a molecular weight of approximately 130 kD involved in signal transduction. IL-6 and the IL-6 receptor form an IL-6/IL-6 receptor complex, which then binds to gp130 so that the biological activity of IL-6 is transduced into the cell (Non Patent Literature 6).

Patent Literature 1 describes various forms of an anti-IL-6R (IL-6 receptor) antibody, for example, a humanized anti-IL-6R antibody and a chimeric anti-IL-6R antibody. Patent Literature 2 describes a therapeutic agent for chronic rheumatoid arthritis and a synovial cell growth inhibitor comprising an IL-6 antagonist such as an anti-IL-6R antibody as an active ingredient. Patent Literature 3 describes the treatment of diseases caused by IL-6 production, such as plasmacytosis, hyperimmunoglobulinemia, anemia, nephritis, cachexia, rheumatism, Castleman's disease, and mesangial nephritis. Patent Literature 4 describes a preventive or therapeutic agent for diseases involving sensitized T cells, for example, multiple sclerosis, uveitis, chronic thyroiditis, delayed-type hypersensitivity, contact dermatitis, and atopic dermatitis, comprising an anti-IL-6R antibody as an active ingredient.

Patent Literature 5 describes a therapeutic agent for systemic lupus erythematosus comprising an anti-IL-6R antibody as an active ingredient. Patent Literature 6 describes a therapeutic agent for Crohn disease comprising an anti-IL-6R antibody as an active ingredient. Patent Literature 7 describes a therapeutic agent for pancreatitis comprising an anti-IL-6R antibody as an active ingredient. Patent Literature 8 describes a therapeutic agent for psoriasis comprising an anti-IL-6R antibody as an active ingredient. Patent Literature 9 describes a therapeutic agent for chronic arthritis in childhood comprising an anti-IL-6R antibody as an active ingredient. Patent Literature 10 describes an inhibitor of nerve invasion by cells, comprising an anti-IL-6R antibody as an active ingredient and states that nerve invasion in human pancreatic cancer can be inhibited.

As mentioned above, antibodies against the IL-6 receptor are used in the treatment of inflammatory diseases such as rheumatism. However, whether or not IL-6 inhibitors are effective for the treatment of other diseases such as schizophrenia is unknown because inflammatory cytokines such as IL-6 form a complicated network.

Schizophrenia is mental illness characterized by various symptoms (e.g., positive symptoms (delusions, hallucinations, thought disorders, etc.), negative symptoms, and cognitive impairment). Although there are drugs ameliorating symptoms such as hallucinations and delusions in schizophrenia, any radical treatment method therefor has not yet been developed.

As for the relation of schizophrenia to cytokines, it has been reported that IL-6 concentrations are increased in the peripheral blood, cerebrospinal fluids, and the like of schizophrenia patients as compared with healthy individuals (Non Patent Literatures 7 to 10). Maternal immune activation (MIA) is considered as one of the environmental factors in the occurrence of schizophrenia. In mice, MIA during pregnancy is known to influence the development of the fetal brain and result in offspring having abnormal behavior. It has been reported that IL-6 is involved in this phenomenon (Non Patent Literature 11).

Animal models of schizophrenia have been prepared by feeding with a high fat diet, and their characters have been analyzed. For example, it has been reported that in rats, the levels of inflammatory cytokines including IL-6 are increased in blood by high fat diet feeding (Non Patent Literature 12). It has also been reported that in mice, prepulse inhibition (in the present specification, also referred to as PPI) is deteriorated by high fat diet feeding in a period at or around puberty (Non Patent Literature 13). In this context, PPI means a phenomenon in which startle response is drastically inhibited by preceding very weak stimulus (prepulse) immediately before startle stimulus (pulse). PPI is known to serve as an index for sensorimotor gating. In schizophrenia, it is thought that unnecessary signals are excessively transduced to the cerebral cortex due to failure in sensorimotor gating, which is partly responsible for causing symptoms such as thought disorders.

It has also been reported that the deterioration of PPI is a physiological abnormality also seen in Tourette syndrome, obsessive compulsive neurosis, blepharospasm, enuresis (enuresis nocturna), posttraumatic stress disorder, and use of stimulant drugs such as amphetamine or narcotics such as ketamine (Non Patent Literatures 14 and 15). Tourette syndrome occurs before the age of 18 years and manifests both vocal tic and motor tic with a chronic course in a group of neurodevelopmental disorders that manifest tics (sudden, rapid, repetitive, and non-rhythmic motor or vocal). Obsessive compulsive neurosis, also called obsessive compulsive disorder, is mental illness that causes repetitive irrational and unwanted action or thought resulting in waste of time, subjective suffering, impaired social functioning, etc. Blepharospasm causes twitch (excessive blink) of the muscles of the right and left eyelids which are then difficult to open. This condition is a focal dystonia which is involuntary movement, and is progressive. Any radical treatment method for these mental illnesses has not yet been developed.

CITATION LIST

Patent Literature

Patent Literature 1: WO92/19759
Patent Literature 2: WO96/11020
Patent Literature 3: WO96/12503
Patent Literature 4: WO98/42377
Patent Literature 5: WO98/42377
Patent Literature 6: WO99/47170
Patent Literature 7: WO00/10607
Patent Literature 8: WO02/3492
Patent Literature 9: WO02/080969
Patent Literature 10: WO2009/148148

Non Patent Literature

Non Patent Literature 1: Hirano, T. et al., Nature (1986) 324, 73-76
Non Patent Literature 2: Akira, S. et al., Adv. in Immunology (1993) 54, 1-78
Non Patent Literature 3: Lotz, M. et al., J. Exp. Med. (1988) 167, 1253-1258
Non Patent Literature 4: Taga, T. et al., J. Exp. Med. (1987) 166, 967-981
Non Patent Literature 5: Yamasaki, K. et al., Science (1988) 241, 825-828
Non Patent Literature 6: Taga, T. et al., Cell (1989) 58, 573-581
Non Patent Literature 7: Sasayama, D., Wakabayashi, C. et al., J. Psychiatr. Res. (2011) 45(11), 1439-1444
Non Patent Literature 8: Sasayama, D. et al., J. Psychiatr. Res. (2014) 50, 79-83
Non Patent Literature 9: Potvin, S. et al., Biol. Psychiatry (2008) 63, 801-808
Non Patent Literature 10: Noto, C., Ota, V. K. et al., Int. J. Neuropsychopharmacol. (2015) 18 (4): DOI: http://dx.doi.org/10.1093/ijnp/pyu042 First published online: Oct. 31, 2014
Non Patent Literature 11: Smith, S. E. P. et al., J. Neurosci. (2007) 27(40), 10695-10702
Non Patent Literature 12: Cano, P. et al., Obesity (2009) 17, 1866-1871
Non Patent Literature 13: Labouesse, M. A. et al., Psychoneuroendocrinology (2013) 38, 2562-2574
Non Patent Literature 14: Kohl, S. et al., Journal of Psychiatric Research (2013) 47, 445-452
Non Patent Literature 15: Braff D L, Geyer M A, Swerdlow N R, Human studies of prepulse inhibition of startle: normal subjects, patient groups, and pharmacological studies. Psychopharmacology (Berl). 2001 July; 156(2-3):234-58.

SUMMARY OF INVENTION

Technical Problem

As described above, it has been reported that the concentration of IL-6 in blood is increased in schizophrenia. However, the levels of other cytokines are also increased, and the detailed roles of IL-6 and an IL-6 receptor in the occurrence of schizophrenia have not been revealed. Also, Non Patent Literature 11 discloses, for example, that: the administration of IL-6 to a mother causes abnormalities in prepulse inhibition and latent inhibition in newborn mice; the administration of an anti-IL-6 antibody to a mother can prevent the abnormal behavior of offspring caused by MIA; and in mice, IL-6 is important for the development of the fetal brain in relation to MIA. However, any role of IL-6 in the occurrence of schizophrenia after birth has not been shown. Thus, how the administration of an IL-6 inhibitor is effective for schizophrenia is totally unknown.

The detailed roles of IL-6 and an IL-6 receptor in the occurrence of Tourette syndrome and obsessive compulsive neurosis have not been revealed. Thus, how the administration of an IL-6 inhibitor is effective for Tourette syndrome and obsessive compulsive neurosis is totally unknown.

The present invention has been made in light of such situations. An object of the present invention is to provide a novel therapeutic agent for mental illness.

Solution to Problem

The present inventors have conducted diligent studies to attain the objects. As a result, the present inventors have found that an anti-IL-6 receptor antibody remarkably suppresses the deterioration of prepulse inhibition, and completed the present invention.

More specifically, the present invention provides the following [1] to [28]:

[1] A therapeutic agent for mental illness comprising an interleukin 6 (IL-6) inhibitor as an active ingredient.
[2] The therapeutic agent for mental illness according to [1], wherein the IL-6 inhibitor is an IL-6 receptor inhibitor.
[3] The therapeutic agent for mental illness according to [1], wherein the IL-6 inhibitor is an anti-IL-6 receptor antibody.
[4] The therapeutic agent for mental illness according to [3], wherein the anti-IL-6 receptor antibody is a chimeric antibody, a humanized antibody, or a human antibody.
[5] The therapeutic agent for mental illness according to any of [1] to [4], wherein the therapeutic agent suppresses the attenuation of a prepulse inhibitory effect.
[6] The therapeutic agent for mental illness according to any of [1] to [5], wherein the mental illness is schizophrenia, Tourette syndrome, and/or obsessive compulsive neurosis.
[7] The therapeutic agent for mental illness according to [3], wherein the anti-IL-6 receptor antibody is PM-1 antibody.
[8] A method for treating or preventing mental illness in a subject, the method comprising the step of administering an effective amount of an interleukin 6 (IL-6) inhibitor to the subject having mental illness or the subject having the potential to develop mental illness.
[9] The method according to [8], wherein the IL-6 inhibitor is an IL-6 receptor inhibitor.
[10] The method according to [8], wherein the IL-6 inhibitor is an anti-IL-6 receptor antibody.
[11] The method according to [10], wherein the anti-IL-6 receptor antibody is a chimeric antibody, a humanized antibody, or a human antibody.
[12] The method according to any of [8] to [11], wherein the method suppresses the attenuation of a prepulse inhibitory effect.
[13] The method according to any of [8] to [12], wherein the mental illness is schizophrenia, Tourette syndrome, and/or obsessive compulsive neurosis.
[14] The method according to [3], wherein the anti-IL-6 receptor antibody is PM-1 antibody.

[15] An interleukin 6 (IL-6) inhibitor for the treatment of mental illness.
[16] The IL-6 inhibitor according to [15], wherein the IL-6 inhibitor is an IL-6 receptor inhibitor.
[17] The IL-6 inhibitor according to [15], wherein the IL-6 inhibitor is an anti-IL-6 receptor antibody.
[18] The IL-6 inhibitor according to [17], wherein the anti-IL-6 receptor antibody is a chimeric antibody, a humanized antibody, or a human antibody.
[19] The IL-6 inhibitor according to any of [15] to [18], wherein the IL-6 inhibitor suppresses the attenuation of a prepulse inhibitory effect.
[20] The IL-6 inhibitor according to any of [15] to [19], wherein the mental illness is schizophrenia, Tourette syndrome, and/or obsessive compulsive neurosis.
[21] The IL-6 inhibitor according to [17], wherein the anti-IL-6 receptor antibody is PM-1 antibody.
[22] Use of an interleukin 6 (IL-6) inhibitor for the production of a therapeutic agent for mental illness.
[23] The use according to [22], wherein the IL-6 inhibitor is an IL-6 receptor inhibitor.
[24] The use according to [22], wherein the IL-6 inhibitor is an anti-IL-6 receptor antibody.
[25] The use according to [24], wherein the anti-IL-6 receptor antibody is a chimeric antibody, a humanized antibody, or a human antibody.
[26] The use according to any of [22] to [25], wherein the IL-6 inhibitor suppresses the attenuation of a prepulse inhibitory effect.
[27] The use according to any of [22] to [26], wherein the mental illness is schizophrenia, Tourette syndrome, and/or obsessive compulsive neurosis.
[28] The use according to [24], wherein the anti-IL-6 receptor antibody is PM-1 antibody.

Advantageous Effects of Invention

The present invention can provide a novel approach for treating mental illness such as schizophrenia, Tourette syndrome, or obsessive compulsive neurosis by ameliorating abnormal sensorimotor gating in the mental illness.

DESCRIPTION OF EMBODIMENTS

Figure 1:
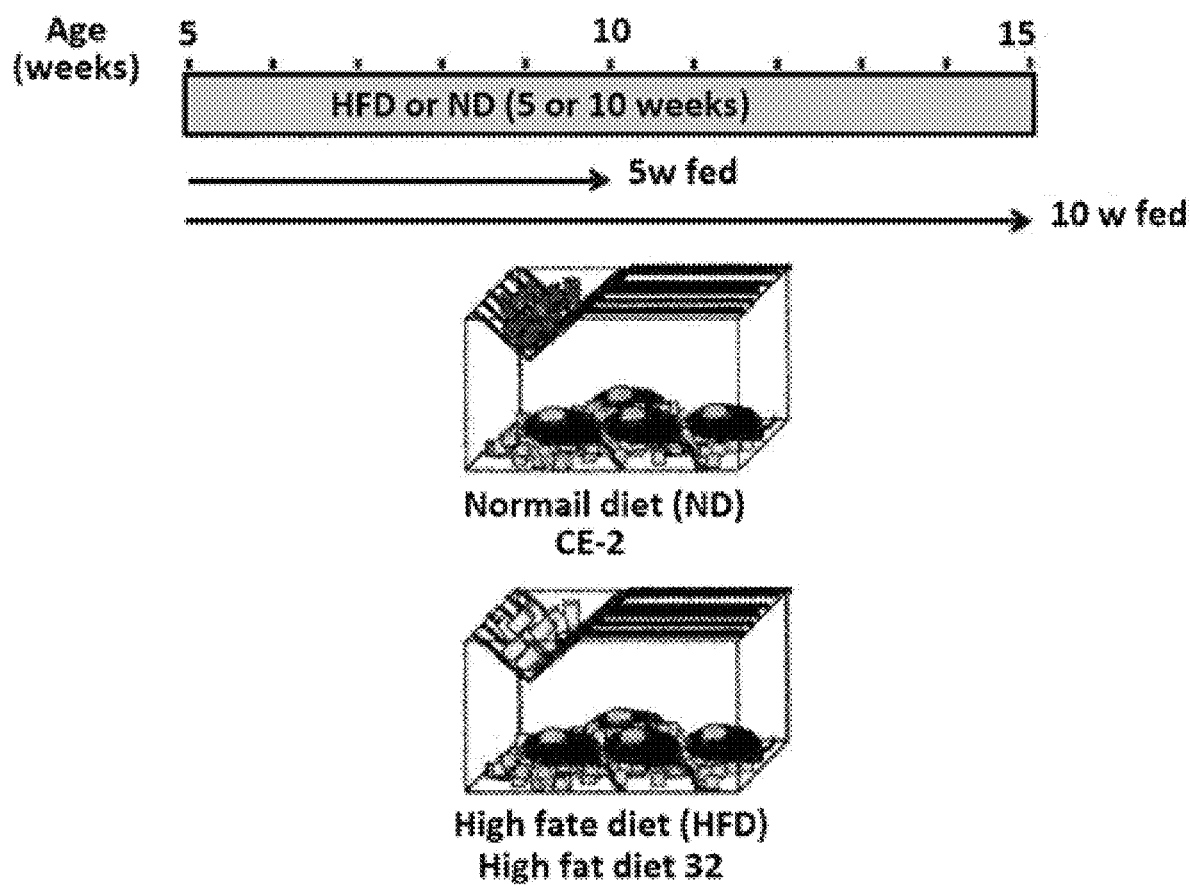
FIG. 1 is a diagram showing a feeding schedule in a high fat diet feeding experiment on male C57B6/J mice.
Figure 2:
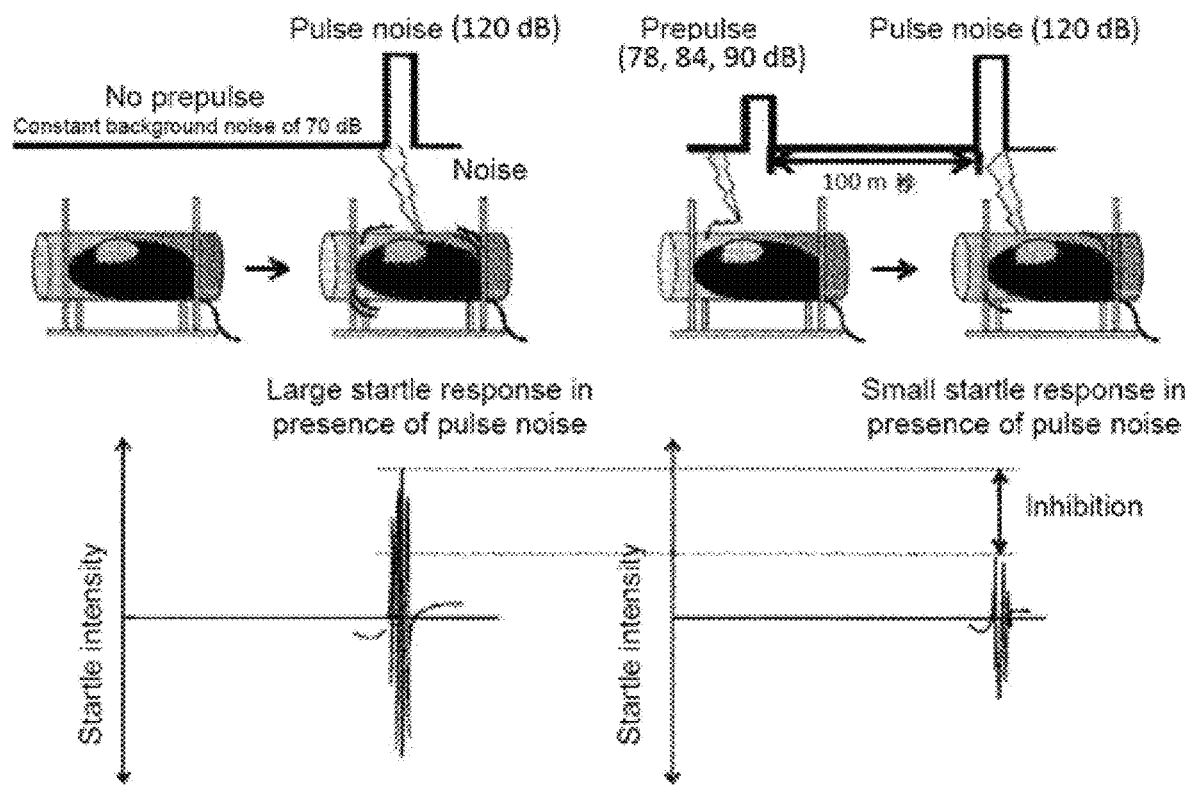
FIG. 2 is a schematic diagram illustrating prepulse inhibition in acoustic startle response.

In the present invention, the "IL-6 inhibitor" is a substance that blocks IL-6 signal transduction and inhibits the biological activity of IL-6. Specific examples of the IL-6 inhibitor can include a substance binding to IL-6, a substance binding to an IL-6 receptor, and a substance binding to gp130. Other examples of the IL-6 inhibitor can include a substance inhibiting STAT3 phosphorylation important as the intracellular signal of IL-6, for example, AG490. The IL-6 inhibitor includes, but is not particularly limited to, an anti-IL-6 antibody, an anti-IL-6 receptor antibody, an anti-gp130 antibody, an IL-6 variant, a soluble IL-6 receptor variant, a partial IL-6 peptide, a partial IL-6 receptor peptide, and a low-molecular compound exhibiting activity similar thereto.

Examples of the preferred form of the IL-6 inhibitor can include an IL-6 receptor inhibitor, particularly an anti-IL-6 receptor antibody.

In the present invention, the "IL-6 receptor inhibitor" is a substance that blocks IL-6 receptor-mediated signal transduction and inhibits the biological activity of the IL-6 receptor. The IL-6 receptor inhibitor may be a substance directly inhibiting the biological activity of an IL-6 receptor by binding to the IL-6 receptor or may be a substance indirectly inhibiting the biological activity of an IL-6 receptor by binding to other substances such as gp130. The IL-6 receptor inhibitor is preferably a substance having the activity of inhibiting the binding between IL-6 and an IL-6 receptor by binding to the IL-6 receptor.

Examples of the IL-6 receptor inhibitor of the present invention include, but are not particularly limited to, an anti-IL-6 receptor antibody, a soluble IL-6 receptor variant, a partial IL-6 receptor peptide, and a low-molecular substance exhibiting activity similar thereto. Preferred examples of the IL-6 receptor inhibitor of the present invention can include an antibody recognizing an IL-6 receptor.

The origin of the anti-IL-6 receptor antibody used in the present invention is not particularly limited, and a mammal-derived antibody is preferred.

The anti-IL-6 receptor antibody used in the present invention can be obtained as a polyclonal or monoclonal antibody by use of an approach known in the art. The anti-IL-6 receptor antibody used in the present invention is particularly preferably a mammal-derived monoclonal antibody. The mammal-derived monoclonal antibody includes an antibody produced by a hybridoma, and an antibody produced by a host transformed with an expression vector containing an antibody gene by a genetic engineering approach, or the like. This antibody inhibits the binding of IL-6 to an IL-6 receptor and blocks the intracellular transduction of the biological activity of IL-6, through its binding to the IL-6 receptor.

Examples of such an antibody include MR16-1 antibody (Tamura, T. et al. Proc. Natl. Acad. Sci. USA (1993) 90, 11924-11928), PM-1 antibody (Hirata, Y. et al., J. Immunol. (1989) 143, 2900-2906), AUK12-20 antibody, AUK64-7 antibody, and AUK146-15 antibody (International Publication No. WO 92-19759), and tocilizumab. Among them, preferred examples of the monoclonal antibody against the human IL-6 receptor include, but are not limited to, the PM-1 antibody and tocilizumab, and preferred examples of the monoclonal antibody against the mouse IL-6 receptor include, but are not limited to, the MR16-1 antibody.

Basically, the anti-IL-6 receptor monoclonal antibody-producing hybridoma can be prepared by use of a technique known in the art as follows: an IL-6 receptor is used as a sensitizing antigen in immunization according to an ordinary immunization method, and the resulting immunocytes can be fused with parent cells known in the art by an ordinary cell fusion method and screened for monoclonal antibody-producing cells by an ordinary screening method to prepare monoclonal antibody-producing hybridomas.

Specifically, the anti-IL-6 receptor antibody can be prepared as follows: for example, the antibody is obtained by using the gene encoding an IL-6 receptor disclosed in European Patent Application Publication No. EP 325474 as a human IL-6 receptor for use as a sensitizing antigen or disclosed in Japanese Patent Laid-Open No. 3-155795 as a mouse IL-6 receptor for use as a sensitizing antigen, and/or the amino acid sequence.

IL-6 receptor proteins are classified into two types: a protein expressed on the cell membrane, and a protein dissociated from the cell membrane (soluble IL-6 receptor) (Yasukawa, K. et al., J. Biochem. (1990) 108, 673-676). The soluble IL-6 receptor is constituted by substantially the extracellular region of the IL-6 receptor bound with the cell membrane and differs from the membrane-bound IL-6 receptor in that the soluble IL-6 receptor is deficient in the transmembrane region or in the transmembrane region and the intracellular region. Any IL-6 receptor may be used as the IL-6 receptor protein of the present invention as long as the IL-6 receptor may be used as a sensitizing antigen in the preparation of the anti-IL-6 receptor antibody used in the present invention.

The gene sequence of the IL-6 receptor is inserted to an expression vector system known in the art, and appropriate host cells are transformed therewith. Then, the IL-6 receptor protein of interest is purified by a method known in the art from the inside of the host cells or from a culture supernatant thereof. This purified IL-6 receptor protein can be used as the sensitizing antigen. Alternatively, cells expressing the IL-6 receptor or a fusion protein of the IL-6 receptor protein with another protein may be used as the sensitizing antigen.

The mammal to be immunized with the sensitizing antigen is not particularly limited and is preferably selected in consideration with compatibility with the parent cells for use in cell fusion. In general, a rodent, for example, a mouse, a rat, or a hamster is used.

The animal is immunized with the sensitizing antigen according to a method known in the art. For example, a general method involves intraperitoneally or subcutaneously injecting the sensitizing antigen to the mammal. Specifically, the sensitizing antigen diluted or suspended in an appropriate amount with or in PBS (phosphate-buffered saline), saline, or the like is mixed, if desired, with an appropriate amount of a usual adjuvant, for example, a complete Freund's adjuvant. After emulsification, several shots of the emulsion are each preferably administered to the mammal every 4 to 21 days. Also, an appropriate carrier can be used in the immunization with the sensitizing antigen.

After such immunization and confirmation of a rise in desired antibody level in serum, immunocytes are collected from the mammal and subjected to cell fusion. Preferred examples of the immunocytes that are subjected to cell fusion particularly include spleen cells.

Mammalian myeloma cells for use as partner parent cells to be fused with the immunocytes have already been known in the art, and various cell lines, for example, P3X63Ag8.653 (Kearney, J. F. et al., J. Immunol. (1979) 123, 1548-1550), P3X63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S. J. Exp. Med. (1978) 148, 313-323), and R210 (Galfre, G. et al., Nature (1979) 277, 131-133) are appropriately used.

Basically, the cell fusion between the immunocytes and the myeloma cells can be carried out according to a method known in the art, for example, the method of Milstein et al. (Kohler. G. and Milstein, C., Methods Enzymol. (1981) 73, 3-46).

More specifically, the cell fusion is carried out, for example, in a usual nutrient medium in the presence of a cell fusion promoter. For example, polyethylene glycol (PEG) or hemagglutinating virus of Japan (HVJ) is used as the fusion promoter. An auxiliary such as dimethyl sulfoxide can be further added thereto and used, if desired, for enhancing fusion efficiency.

The ratio between the immunocytes and the myeloma cells used is preferably set to, for example, 1:1 to 10:1 (immunocytes:myeloma cells). For example, an RPMI1640 medium or a MEM medium suitable for the growth of the myeloma cell lines mentioned above or a usual medium for use in this kind of cell culture can be used as the medium in the cell fusion and may be used in combination with a serum supplement such as fetal calf serum (FCS).

For the cell fusion, predetermined amounts of the immunocytes and the myeloma cells are well mixed in the medium. A PEG solution, for example, a solution of PEG having an average molecular weight on the order of 1000 to 6000, preheated to approximately 37° C. is usually added to the mixture at a concentration of 30 to 60% (w/v) and mixed therewith to form the fusion cells (hybridomas) of interest. Subsequently, the operation of sequentially adding an appropriate medium and removing a supernatant by centrifugation can be repeated to remove cell fusion agents or the like unfavorable for the growth of the hybridomas.

The hybridomas thus obtained are cultured in a usual selective medium, for example, a HAT medium (medium containing hypoxanthine, aminopterin, and thymidine) for selection. This culture in the HAT medium is continued for a period (usually, several days to several weeks) sufficient for killing cells (non-fused cells) other than the hybridomas of interest. Subsequently, hybridomas producing the antibody of interest are screened for and cloned by an ordinary limiting dilution method.

In addition to such obtainment of the hybridomas by the immunization of the non-human animal with the antigen, a desired human antibody having binding activity against the desired antigen or cells expressing the antigen may be obtained by sensitizing in vitro human lymphocytes with the desired antigen protein or cells expressing the antigen and fusing the sensitized B lymphocytes with human myeloma cells, for example, U266 (see Japanese Patent Publication No. 1-59878). Alternatively, the antigen or cells expressing the antigen may be administered to a transgenic animal having human antibody gene repertoires, and the desired human antibody can be obtained according to the method mentioned above (see International Publication Nos. WO93/12227, WO92/03918, WO94/02602, WO94/25585, WO96/34096, and WO96/33735).

The monoclonal antibody-producing hybridomas thus prepared can be subcultured in a usual medium and can also be preserved for a long period in liquid nitrogen.

The monoclonal antibody is obtained from the hybridomas by the adoption of, for example, a method which involves culturing the hybridomas according to an ordinary method and obtaining the antibody as a culture supernatant thereof, or a method which involves administering the hybridomas to mammals compatible therewith and, after growth, obtaining the antibody as ascitic fluid thereof. The former method is suitable for obtaining a highly pure antibody, while the latter method is suitable for the large-scale production of the antibody.

For example, hybridomas producing the anti-IL-6 receptor antibody can be prepared by a method disclosed in Japanese Patent Laid-Open No. 3-139293. This preparation can be carried out by a method which involves intraperitoneally injecting PM-1 antibody-producing hybridomas BALB/c mice to obtain ascitic fluid, from which the PM-1 antibody is purified, or a method which involves culturing the hybridomas in an appropriate medium, for example, an RPMI1640 medium containing 10% fetal calf serum and 5% BM-Condimed H1 (manufactured by Boehringer Mannheim), a Hybridoma SFM medium (manufactured by Gibco BRL/Life Technologies, Inc.), or a PFHM-II medium (manufactured by Gibco BRL/Life Technologies, Inc.) and purifying the PM-1 antibody from the culture supernatant.

In the present invention, a recombinant antibody produced by use of a gene recombination technique which involves cloning an antibody gene from hybridomas, incorporating the antibody gene into an appropriate vector, and transferring this vector to a host can be used as the monoclonal antibody (see e.g., Borrebaeck C. A. K. and Larrick J. W. THERAPEUTIC MONOCLONAL ANTIBODIES, Published in the United Kingdom by MACMILLAN PUBLISHERS LTD, 1990).

Specifically, mRNAs encoding the variable (V) regions of the antibody are isolated from cells, for example, hybridomas, producing the antibody of interest. For the mRNA isolation, total RNA is prepared by a method known in the art, for example, a guanidine ultracentrifugation method (Chirgwin, J. M. et al., Biochemistry (1979) 18, 5294-5299) or an AGPC method (Chomczynski, P. et al., Anal. Biochem. (1987) 162, 156-159), and the mRNAs are prepared using mRNA Purification Kit (manufactured by Pharmacia Corp.) or the like. Alternatively, the mRNAs can be directly prepared by use of QuickPrep mRNA Purification Kit (manufactured by Pharmacia Corp.).

Antibody V region cDNAs are synthesized from the obtained mRNAs using reverse transcriptase. The cDNA synthesis can be carried out using AMV Reverse Transcriptase First-strand cDNA Synthesis Kit or the like. Also, 5'-Ampli FINDER RACE Kit (manufactured by Clontech Laboratories, Inc.) and a PCR-based 5'-RACE method (Frohman, M. A. et al., Proc. Natl. Acad. Sci. USA (1988) 85, 8998-9002; and Belyavsky, A. et al., Nucleic Acids Res. (1989) 17, 2919-2932) can be used in the cDNA synthesis and amplification. The DNA fragments of interest are purified from the obtained PCR products and ligated with vector DNAs. Recombinant vectors are thereby prepared and transferred to E. coli or the like. Colonies are selected to prepare desired recombinant vectors. The nucleotide sequences of the DNAs of interest are confirmed by a method known in the art, for example, a deoxy method.

If DNAs encoding the V regions of the antibody of interest are obtained, these DNAs are linked to DNAs encoding constant regions (C regions) of a desired antibody, and these linked DNAs are incorporated into expression vectors. Alternatively, the DNAs encoding the antibody V regions may be incorporated into expression vectors containing the DNAs of the antibody C regions.

For the production of the antibody used in the present invention, the antibody gene is incorporated into an expression vector such that the antibody gene is expressed under the control of expression control regions, for example, an enhancer and a promoter, as mentioned later. Next, host cells are transformed with this expression vector, and the antibody can be expressed.

In the present invention, a gene recombinant antibody that has been artificially engineered for the purpose of, for example, reducing the heterologous antigenicity against humans, for example, a chimeric antibody or a humanized antibody, can be used. Such an engineered antibody can be produced by use of a known method.

The chimeric antibody is obtained by linking the antibody V region-encoding DNAs obtained as described above to human antibody C region-encoding DNAs, and incorporating the linked DNAs into expression vectors, which are then transferred to a host, followed by the production of the antibody (see European Patent Application Publication No. EP125023 and International Publication No. WO92-19759). A chimeric antibody useful in the present invention can be obtained by use of this known method.

The humanized antibody, also called reshaped human antibody, is obtained by grafting the complementarity-determining regions (CDRs) of a non-human mammalian antibody, for example, a mouse antibody, to the complementarity-determining regions of a human antibody. A general gene recombination approach therefor is also known (see European Patent Application Publication No. EP125023 and International Publication No. WO92-19759).

Specifically, DNA sequences designed so as to link mouse antibody CDRs and human antibody framework regions (FRs) are synthesized by PCR using several prepared oligonucleotides having terminal portions overlapping with each other. The obtained DNAs are linked to DNAs encoding human antibody C regions. Subsequently, the linked DNAs are incorporated into expression vectors, which are then transferred to a host, followed by the production of the antibody to obtain the humanized antibody (see European Patent Application Publication No. EP239400 and International Publication No. WO92-19759).

The human antibody FRs to be connected via CDRs are selected such that the complementarity-determining regions form a favorable antigen-binding site. If necessary, amino acids in the framework regions of the antibody variable regions may be substituted such that the complementarity-determining regions of the resulting reshaped human antibody form an appropriate antigen-binding site (Sato, K. et al., Cancer Res. (1993) 53, 851-856).

Usually, human antibody C regions are used for the chimeric antibody or the humanized antibody. Examples of the human antibody heavy chain C region include C$\gamma$, C$\alpha$, C$\mu$, C$\delta$, C$\epsilon$. For example, C$\gamma$1, C$\gamma$2, C$\gamma$3, or C$\gamma$4 can be used. Examples of the human antibody light chain C region can include $\kappa$ and $\lambda$. These human antibody C regions may be modified in order to improve the stability of the antibody or the stability of production thereof.

The chimeric antibody is composed of the variable regions of a non-human mammal-derived antibody and human antibody-derived C regions. The humanized antibody is composed of the complementarity-determining regions of a non-human mammal-derived antibody and human antibody-derived framework regions and C regions.

These antibodies exhibit reduced antigenicity in human bodies and as such, are useful as antibodies for use in the present invention.

Specific examples of the humanized antibody used in the present invention include humanized PM-1 antibodies (tocilizumab) (see International Publication No. WO92-19759). Alternatively, the humanized antibody may be a substitution variant derived from the humanized PM-1 antibody by the substitution, deletion, addition, or the like of its amino acid sequence.

In addition to the aforementioned methods for obtaining a human antibody, a technique of obtaining a human antibody by panning using a human antibody library is also known. For example, human antibody variable regions are expressed as a single-chain antibody (scFv) on the surface of phages by a phage display method, and a phage binding to the antigen may be selected. The gene of the selected phage can be analyzed to determine DNA sequences encoding the variable regions of the human antibody binding to the antigen. If the DNA sequence of scFv binding to the antigen is revealed, an appropriate expression vector containing this sequence can be prepared to obtain the human antibody. These methods have already been well known. See WO92/01047, WO92/20791, WO93/06213, WO93/11236, WO93/19172, WO95/01438, and WO95/15388.

The antibody gene constructed as described above can be expressed by a method known in the art. In the case of using mammalian cells, the antibody gene can be expressed by use of a DNA in which a useful promoter routinely used, the antibody gene to be expressed, and a poly-A signal 3'-downstream thereof are functionally linked, or a vector containing the DNA. Examples of the promoter/enhancer can include human cytomegalovirus immediate early promoter/enhancer.

Alternatively, a promoter/enhancer of a virus such as retrovirus, polyoma virus, adenovirus, or simian virus 40 (SV40), a mammalian cell-derived promoter/enhancer such as human elongation factor 1α (HEF1α), or the like can be used as the promoter/enhancer for the antibody expression used in the present invention.

In the case of using, for example, the SV40 promoter/enhancer, the antibody expression can be readily carried out according to the method of Mulligan et al. (Mulligan, R. C. et al., Nature (1979) 277, 108-114). In the case of using the HEF1α promoter/enhancer, the antibody expression can be readily carried out according to the method of Mizushima et al. (Mizushima, S. and Nagata, S. Nucleic Acids Res. (1990) 18, 5322).

In the case of using prokaryotic cells as the host, bacterial cells can be used in the production system. $E.$ $coli$ or $Bacillus$ $subtilis$ is known as the bacterial cells.

For $E.$ $coli$, a useful promoter routinely used, a signal sequence for antibody secretion, and the antibody gene to be expressed can be functionally linked and expressed. Examples of the promoter can include lacZ promoter and araB promoter. In the case of using the lacZ promoter, the antibody expression can be carried out according to the method of Ward et al. (Ward, E. S. et al., Nature (1989) 341, 544-546; and Ward, E. S. et al. FASEB J. (1992) 6, 2422-2427). In the case of using the araB promoter, the antibody expression can be carried out according to the method of Better et al. (Better, M. et al. Science (1988) 240, 1041-1043).

In the case of production in the periplasm of $E.$ $coli$, pelB signal sequence (Lei, S. P. et al., J. Bacteriol. (1987) 169, 4379-4383) can be used as the signal sequence for antibody secretion. The antibody produced in the periplasm is separated and then used after appropriate refolding of the antibody structure (see e.g., WO96/30394).

A replication origin derived from SV40, polyoma virus, adenovirus, bovine papillomavirus (BPV), or the like can be used. The expression vector can contain a selective marker such as aminoglycoside phosphotransferase (APH) gene, thymidine kinase (TK) gene, $E.$ $coli$ xanthine guanine phosphoribosyltransferase (Ecogpt) gene, or dihydrofolate reductase (dhfr) gene in order to increase the number of gene copies in the host cell system.

For the production of the antibody used in the present invention, an arbitrary production system can be used. The production system for the antibody production is any of in vitro and in vivo production systems. Examples of the in vitro production system include a production system using eukaryotic cells and a production system using prokaryotic cells.

In the case of using eukaryotic cells as the host, animal cells, plant cells, or fungal cells can be used in the production system. (1) Mammalian cells, for example, CHO, COS, myeloma, BHK (baby hamster kidney), HeLa, and Vero, (2) amphibian cells, for example, $Xenopus$ oocytes, or (3) insect cells, for example, sf9, sf21, and Tn5 are known as the animal cells. $Nicotiana$ $tabacum$-derived cells are known as the plant cells and can be callus-cultured. Yeasts of, for example, the genus $Saccharomyces$ (e.g., $Saccharomyces$ $cerevisiae$) or filamentous fungi of, for example, the genus $Aspergillus$ (e.g., $Aspergillus$ $niger$) are known as the fungal cells.

The antibody gene of interest is transferred to these cells by transformation, and the transformed cells are cultured in vitro to obtain the antibody. This culture is carried out according to a method known in the art. For example, DMEM, MEM, RPMI1640, or IMDM can be used as a medium and may be used in combination with a serum supplement such as fetal calf serum (FCS). Alternatively, the cells thus harboring the antibody gene may be transferred to the peritoneal cavity or the like of an animal so that the antibody is produced in vivo.

On the other hand, examples of the in vivo production system include a production system using an animal and a production system using a plant. In the case of using the animal, a mammal, an insect, or the like can be used in the production system.

A goat, a pig, sheep, a mouse, cattle, or the like can be used as the mammal (Vicki Glaser, SPECTRUM Biotechnology Applications, 1993). A silkworm can be used as the insect. In the case of using the plant, for example, tobacco can be used.

The antibody gene is transferred to such an animal or a plant, and the antibody is produced in the body of the animal or the plant and recovered. For example, the antibody gene is prepared as a fusion gene by insertion in frame into a gene encoding a protein specifically produced in milk, such as goat β casein. A DNA fragment having the fusion gene of the inserted antibody gene is injected into a goat embryo, and this embryo is introduced into a female goat. The desired antibody is obtained from milk produced by a transgenic goat born from the embryo-recipient goat, or progeny thereof. Hormone may be appropriately used for the transgenic goat in order to increase the amount of the milk containing the desired antibody produced by the transgenic goat (Ebert, K. M. et al., Bio/Technology (1994) 12, 699-702).

In the case of using the silkworm, the silkworm is infected with baculovirus having an insert of the antibody gene of interest, and the desired antibody is obtained from the body fluid of this silkworm (Maeda, S. et al., Nature (1985) 315, 592-594). In the case of using the tobacco, the antibody gene of interest is inserted to a vector for expression in plants, for example, pMON530, and this vector is transferred to a bacterium such as *Agrobacterium tumefaciens*. Tobacco, for example, *Nicotiana tabacum*, is infected with this bacterium, and the desired antibody is obtained from the leaf of this tobacco (Julian, K.-C. Ma et al., Eur. J. Immunol. (1994)24, 131-138).

In the case of producing the antibody in the in vitro or in vivo production system as mentioned above, an antibody heavy chain (H chain)-encoding DNA and an antibody light chain (L chain)-encoding DNA may be incorporated into separate expression vectors, and the host can be co-transformed with these expression vectors. Alternatively, the H chain-encoding DNA and the L chain-encoding DNA may be incorporated into a single expression vector, and the host can be transformed with this expression vector (see International Publication No. WO94-11523).

The antibody used in the present invention may be a fragment of the antibody or a modified form of the antibody as long as the fragment or the modified form can be suitably used in the present invention. Examples of the antibody fragment include Fab, F(ab')$_2$, Fv, and single-chain Fv (scFv) containing H and L chain Fvs linked through an appropriate linker.

Specifically, the antibody fragment is formed by the treatment of the antibody with an enzyme, for example, papain or pepsin, or is expressed in appropriate host cells after construction of a gene encoding the antibody fragment and subsequent transfer of this gene to an expression vector (see e.g., Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 497-515; Lamoyi, E., Methods in Enzymology (1989) 121, 652-663; Rousseaux, J. et al., Methods in Enzymology (1989) 121, 663-66; and Bird, R. E. et al., TIBTECH (1991) 9, 132-137).

The scFv is obtained by linking the H chain V region and the L chain V region of the antibody. In this scFv, the H chain V region and the L chain V region are linked via a linker, preferably a peptide linker (Huston, J. S. et al., Proc. Natl. Acad. Sci. U.S.A. (1988) 85, 5879-5883). The H chain V region and the L chain V region in the scFv may be derived from any of those described above as the antibody according to the present invention. For example, an arbitrary single-chain peptide composed of 12 to 19 amino acid residues is used as the peptide linker for linking the V regions.

A DNA encoding the scFv is obtained by using a DNA encoding the antibody H chain or the H chain V region and a DNA encoding the antibody L chain or the L chain V region as templates to amplify each DNA moiety encoding the desired amino acid sequence, of these sequences, by PCR using a primer pair annealing to both ends thereof, followed by amplification by the combined use of a DNA encoding the peptide linker moiety and a primer pair annealing thereto such that the both ends of the peptide linker are linked to the H chain and the L chain, respectively.

Once the scFv-encoding DNA is prepared, an expression vector containing the DNA, and a host transformed with the expression vector can be obtained according to routine methods. Also, the scFv can be obtained according to a routine method using the host.

These antibody fragments can be expressed through the obtainment of their genes in the same way as above and produced by the host. The "antibody" according to the present invention also encompasses these antibody fragments.

Antibodies bound with various molecules such as polyethylene glycol (PEG) may be used as the modified form of the antibody. The "antibody" according to the present invention also encompasses these modified forms of the antibody. Such a modified form of the antibody can be obtained by the chemical modification of the obtained antibody. These methods have already been established in the art.

The antibody produced and expressed as described above can be separated from the inside or outside of the cells or from the host and purified until homogeneous. The separation and purification of the antibody used in the present invention can be carried out by affinity chromatography. Examples of columns for use in the affinity chromatography include protein A columns and protein G columns. Examples of carriers for use in the protein A columns include Hyper D, POROS, and Sepharose F.F. Any of other ordinary separation and purification methods for use in proteins can be used without limitations.

The antibody used in the present invention can be separated and purified by appropriately selecting or combining, for example, chromatography other than the affinity chromatography, filters, ultrafiltration, salting out, and/or dialysis. Examples of the chromatography include ion-exchange chromatography, hydrophobic chromatography, and gel filtration. These chromatography techniques are applicable to HPLC (high-performance liquid chromatography). Alternatively, reverse-phase HPLC may be used.

The concentration of the antibody thus obtained can be measured by, for example, absorbance measurement or ELISA. Specifically, in the case of measuring the concentration by the absorbance measurement, the absorbance is measured at 280 nm after appropriate dilution of the antibody with PBS(−), and the concentration is calculated with 1 mg/ml as 1.35 OD. Alternatively, the concentration can be measured by ELISA as follows: goat anti-human IgG (manufactured by TAG) diluted to 1 µg/ml with a 0.1 M bicarbonate buffer solution (pH 9.6) is added at 100 µl/well to a 96-well plate (manufactured by Nunc/Thermo Fisher Scientific, Inc.) and incubated overnight at 4° C. to immobilize the antibody thereon. After blocking, an appropriately diluted antibody used in the present invention or a sample containing the antibody, or a preparation human IgG (manufactured by Cappel Laboratories, Inc.) is added thereto at 100 µl/well and incubated at room temperature for 1 hour.

After washing, alkaline phosphatase-labeled anti-human IgG (manufactured by BioSource International, Inc.) diluted 5000-fold is added thereto at 100 µl/well and incubated at room temperature for 1 hour. After washing, a substrate solution is added thereto and incubated. Then, the absorbance is measured at 405 nm using MICROPLATE READER Model 3550 (manufactured by Bio-Rad Laboratories, Inc.) to calculate the concentration of the antibody of interest.

The partial IL-6 receptor peptide is a peptide having a portion or the whole of the amino acid sequence of a region involved in the binding of the IL-6 receptor to IL-6 in the amino acid sequence of the IL-6 receptor. Such a peptide is composed of usually 10 to 80, preferably 20 to 50, more preferably 20 to 40 amino acid residues.

The partial IL-6 receptor peptide can be prepared by identifying the region involved in the binding of the IL-6 receptor to IL-6 in the amino acid sequence of the IL-6 receptor and producing the peptide by a conventionally known method, for example, a genetic engineering approach or a peptide synthesis method on the basis of a portion or the whole of the amino acid sequence of the identified region.

For the preparation of the partial IL-6 receptor peptide by the genetic engineering approach, a DNA sequence encoding the desired peptide is incorporated into an expression vector, and the partial IL-6 receptor peptide can be obtained according to the aforementioned expression, production, and purification methods for the recombinant antibody.

For the preparation of the partial IL-6 receptor peptide by the peptide synthesis method, a method usually used in peptide synthesis, for example, a solid-phase synthesis method or a liquid-phase synthesis method can be used.

Specifically, the peptide synthesis can be carried out according to methods described in Zoku Iyakuhin no Kaihatsu (Development of Pharmaceuticals, Second Series, in English), Vol. 14, Peptide Synthesis, edited by Haruaki Yajima, Hirokawa Shoten Co., Ltd. (1991). The solid-phase synthesis method used is a method which involves, for example, coupling an amino acid corresponding to the C terminus of the peptide to be synthesized to a support insoluble in an organic solvent, and elongating a peptide chain by alternately repeating the reaction of condensing one by one amino acids (their α-amino groups and side chain functional groups have been protected with appropriate protective groups) in a direction from the C terminus toward the N terminus and the reaction of eliminating the protective groups of the α-amino groups of the amino acids or peptide bound onto the resin. The solid-phase peptide synthesis method is broadly divided into Boc and Fmoc methods depending on the types of the protective groups used.

After such synthesis of the peptide of interest, deprotection reaction and cleavage reaction of the peptide chain from the support are carried out. In the cleavage reaction of the peptide chain, usually, hydrogen fluoride or trifluoromethanesulfonic acid can be used for the Boc method, and TFA can be used for the Fmoc method. In the Boc method, the protected peptide resin is treated, for example, in the presence of anisole in hydrogen fluoride. Subsequently, protective group elimination and cleavage from the support are carried out to recover the peptide. This peptide is freeze-dried to obtain a crude peptide. On the other hand, in the Fmoc method, deprotection reaction and cleavage reaction of the peptide chain from the support can be carried out by the same operation as above, for example, in TFA.

The obtained crude peptide can be separated and purified by application to HPLC. The peptide can be eluted under the optimum conditions by use of a water-acetonitrile mixed solvent usually used in protein purification. A fraction corresponding to a peak in the obtained profile of chromatography is separated and then freeze-dried. The peptide fraction thus purified is identified by, for example, mass spectrometric molecular weight analysis, amino acid composition analysis, or amino acid sequence analysis.

The therapeutic agent for mental illness of the present invention can be used in the treatment and/or prevention of mental illness such as schizophrenia, Tourette syndrome, or obsessive compulsive neurosis. The therapeutic agent for mental illness of the present invention also includes a preventive agent for mental illness that suppresses the occurrence of mental illness. Thus, in the present invention, the "treatment of mental illness" means the prevention of mental illness such as schizophrenia, Tourette syndrome, or obsessive compulsive neurosis, reduction in the incidence of mental illness such as schizophrenia, Tourette syndrome, or obsessive compulsive neurosis, the treatment of mental illness such as schizophrenia, Tourette syndrome, or obsessive compulsive neurosis, the amelioration of a symptom of mental illness such as schizophrenia, Tourette syndrome, or obsessive compulsive neurosis, etc.

The effect of the IL-6 inhibitor used in the present invention as a therapeutic agent for mental illness can be evaluated by using, for example, signal transduction inhibitory activity as an index, though the evaluation method is not limited thereto. The signal transduction inhibitory activity of the IL-6 inhibitor can be evaluated by a method usually used. Specifically, an IL-6-dependent human myeloma cell (S6B45 or KPMM2), a human Lennert T lymphoma cell line KT3, or IL-6-dependent cells MH60.BSF2 are cultured, and IL-6 is added thereto. The $^{3}$H-thymidine uptake of the IL-6-dependent cells can be measured in the presence of the IL-6 inhibitor. Alternatively, IL-6 receptor-expressing cells U266 are cultured, and $^{125}$I-labeled IL-6 is added thereto. $^{125}$I-labeled IL-6 bound with the IL-6 receptor-expressing cells is measured in the presence of the IL-6 inhibitor. In these assay systems, a group involving the IL-6 inhibitor as well as a negative control group free from the IL-6 receptor inhibitor is established. Results obtained in these groups can be compared to evaluate the IL-6 receptor inhibitory activity of the IL-6 receptor inhibitor.

In one embodiment, the therapeutic agent for mental illness of the present invention suppresses the attenuation of a prepulse inhibitory effect. The prepulse inhibition means a phenomenon in which startle response is drastically inhibited by preceding very weak stimulus (prepulse) immediately before startle stimulus (pulse). The attenuation of the prepulse inhibition is found in both of mental illness (e.g., schizophrenia, Tourette syndrome, and obsessive compulsive neurosis) patients and animal models and is therefore considered as one of the psychophysiological indexes for mental illness such as schizophrenia, Tourette syndrome, or obsessive compulsive neurosis. Also, failure in sensorimotor gating is considered to be partly responsible for causing symptoms such as thought disorders in mental illness. The prepulse inhibition is known to serve as an index for sensorimotor gating. Therefore, a drug suppressing the attenuation of a prepulse inhibitory effect is evaluated as having a therapeutic effect on mental illness such as schizophrenia, Tourette syndrome, or obsessive compulsive neurosis.

The suppression of the attenuation of a prepulse inhibitory effect is evaluated by a test using schizophrenia mouse models as described in Examples mentioned later. Specifically, 8-week-old mice are allowed to freely eat a high fat diet (e.g., High Fat Diet 32 (CLEA Japan, Inc.)) until 11 weeks old to prepare schizophrenia mouse models having the induced deterioration of prepulse inhibition. In the high fat diet feeding period, an IL-6 inhibitor or a vehicle is administered thereto three times (at the age of 8, 9, and 10 weeks) by intraperitoneal injection. At the age of 11 weeks, the prepulse inhibition is measured. Provided that the % rate of prepulse inhibition in the IL-6 inhibitor administration group is higher than that of the negative control group, the IL-6 inhibitor is evaluated as suppressing the attenuation of a prepulse inhibitory effect. The measurement of the prepulse inhibition is performed by a modification of the method of Geyer et al. (Braff D L and Geyer M A, Arch Gen Psychiatry 1990, 47: 181-188). Specifically, an acoustic startle response measurement apparatus for mice is used. The mice are acclimatized to 65-dB background noise for 3 minutes. Then, the acoustic startle response is measured for each individual under conditions of the following sessions 1 to 35: sessions 1 to 5 (120-dB×5 rounds, continuous); sessions 6 to 30 (5 rounds each of five types of sessions (1) no prepulse+120-dB pulse, (2) 78-dB prepulse+120-dB pulse, (3) 84-dB prepulse+120-dB pulse, (4) 90-dB prepulse+120-dB pulse, and (5) no pulse (background), randomly generated at any interval of 15 to 20 seconds); and sessions 31 to 35 (120-dB×5 rounds, continuous). The average value (background) of the sessions (5) of sessions 6 to 30 is subtracted from the respective average startle intensities of the sessions (1) to (4) of sessions 6 to 30, and this value is used as the level of startle. The % rate of prepulse inhibition is calculated according to the following expression:

% rate of prepulse inhibition=100×(Level of startle at 120-dB—Level of startle in the presence of each prepulse)/Level of startle at 120-dB Although not wishing to be bound by any theory, the suppression of the attenuation of a prepulse inhibitory effect by the IL-6 inhibitor is probably based on the specific inhibition of GSK3β hyperphosphorylation in the striatum.

The recipient of the therapeutic agent for mental illness of the present invention is a mammal. The mammal is preferably a human.

The therapeutic agent for mental illness of the present invention may be administered in a pharmaceutical form and can be administered systemically or locally through an oral or parenteral route. For example, intravenous injection such as drip infusion, intramuscular injection, intraperitoneal injection, subcutaneous injection, a suppository, enteroclysis, or an oral enteric-coated agent can be selected, and the administration method can be appropriately selected according to the age and symptoms of a patient. The effective dose is not particularly limited and is selected within the range of 0.01 mg to 100 mg per kg for each dose. Alternatively, a dose of 1 to 1000 mg, preferably 5 to 50 mg, can be selected per patient. Specific examples of the preferred dose and administration method include 0.5 mg to 40 mg, preferably 1 mg to 20 mg, of, for example, an anti-IL-6 receptor antibody, per month (4 weeks) per kg of body weight which is administered in one portion or several divided portions, for example, at a dosing schedule such as twice a week, once a week, once per two weeks, or once per four weeks, and an administration method involving the intraperitoneal injection, intravenous injection such as drip infusion, subcutaneous injection, intramuscular injection, or the like. The dosing schedule may be adjusted in such a way that the dosing interval is extended from twice a week or once a week to once per two weeks, once per three weeks, or once per four weeks while the condition of the patient and trends in the values of blood tests are observed.

The therapeutic agent for mental illness of the present invention may be administered together with at least one known mental illness therapy agent or treatment method. When the mental illness is, for example, schizophrenia, the therapeutic agent for mental illness of the present invention can be administered at the same time or sequentially with a conventional antipsychotic which acts mainly by blocking a dopamine-2 receptor (e.g., chlorpromazine, thioridazine, trifluoperazine, fluphenazine, perphenazine, loxapine, molindone, thiothixene, haloperidol, and pimozide), a second-generation antipsychotic which acts by blocking both of a dopamine receptor and a serotonin receptor (e.g., clozapine, risperidone, olanzapine, quetiapine, ziprasidone, and aripiprazole), a long-acting depot antipsychotic (fluphenazine decanoate, fluphenazine enanthate, haloperidol decanoate, risperidone microspheres, etc.), or the like. When the mental illness is, for example, Tourette syndrome, the therapeutic agent for mental illness of the present invention can also be administered at the same time or sequentially with any of the drugs described above as well as an adrenaline α2 receptor agonist (e.g., clonidine and guanfacine). When the mental illness is, for example, obsessive compulsive neurosis, the therapeutic agent for mental illness of the present invention can also be administered at the same time or sequentially with any of the drugs described above as well as a serotonin reuptake inhibitor (SSRI) (e.g., sertraline, paroxetine, fluoxetine, fluvoxamine, citalopram, and escitalopram). Also, the therapeutic agent for mental illness of the present invention can also be used in combination with mental therapy.

The therapeutic agent for mental illness of the present invention may be supplemented with a pharmaceutically acceptable carrier such as a preservative or a stabilizer. The pharmaceutically acceptable carrier means a material that can be administered together with the drugs described above. Examples of the pharmaceutically acceptable material can include sterile water, saline, stabilizers, excipients, buffers, antiseptics, surfactants, chelating agents (EDTA, etc.), and binders.

In the present invention, examples of the surfactant can include nonionic surfactants. Typical examples thereof can include those having HLB 6 to 18, for example: sorbitan fatty acid esters such as sorbitan monocaprylate, sorbitan monolaurate, and sorbitan monopalmitate; glycerin fatty acid esters such as glycerin monocaprylate, glycerin monomyristate, and glycerin monostearate; polyglycerin fatty acid esters such as decaglyceryl monostearate, decaglyceryl distearate, and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbitol fatty acid esters such as polyoxyethylene sorbitol tetrastearate and polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol, polyoxyethylene polyoxypropylene propyl ether, and polyoxyethylene polyoxypropylene cetyl ether; polyoxyethylene alkyl phenyl ethers such as polyoxyethylene nonyl phenyl ether; polyoxyethylene hydrogenated castor oils such as polyoxyethylene castor oil and polyoxyethylene hydrogenated castor oil (polyoxyethylene hydrogen castor oil); polyoxyethylene beeswax derivatives such as polyoxyethylene sorbitol beeswax; polyoxyethylene lanolin derivatives such as polyoxyethylene lanolin; and polyoxyethylene fatty acid amides such as polyoxyethylene stearic acid amide.

Other examples of the surfactant can include anionic surfactants. Typical examples thereof can include: alkyl sulfates having an alkyl group having 10 to 18 carbon atoms, such as sodium cetyl sulfate, sodium lauryl sulfate, and sodium oleyl sulfate; polyoxyethylene alkyl ether sulfates having an average addition molar number of ethylene oxide of 2 to 4 and having an alkyl group having 10 to 18 carbon atoms, such as sodium lauryl polyoxyethylene ether sulfate; alkyl sulfosuccinic acid ester salts having an alkyl group having 8 to 18 carbon atoms, such as sodium lauryl sulfosuccinate; natural surfactants, for example, lecithin and glycerophospholipid; sphingophospholipids such as sphingomyelin; and sucrose fatty acid esters of fatty acids having 12 to 18 carbon atoms.

The drug of the present invention can be supplemented with one or two or more in combination of these surfactants.

The surfactant for use in the preparation of the present invention is preferably a polyoxyethylene sorbitan fatty acid ester such as polysorbate 20, 40, 60, or 80, particularly preferably polysorbate 20 or 80. Polyoxyethylene polyoxypropylene glycol typified by poloxamer (Pluronic F-68(R), etc.) is also preferred.

The amount of the surfactant added differs depending on the type of the surfactant used. The amount of polysorbate 20 or polysorbate 80 added is generally 0.001 to 100 mg/mL, preferably 0.003 to 50 mg/mL, more preferably 0.005 to 2 mg/mL.

In the present invention, examples of the buffer can include phosphate, citrate buffer solutions, acetate, malate, tartrate, succinate, lactate, potassium phosphate, gluconate, caprylate, deoxycholate, salicylate, triethanolamine, fumarate, other organic acids, carbonate buffer solutions, Tris buffer solutions, histidine buffer solutions, and imidazole buffer solutions.

Also, a solution preparation may be prepared by dissolution in an aqueous buffer solution known in the field of solution preparations. The concentration of the buffer solution is generally 1 to 500 mM, preferably 5 to 100 mM, more preferably 10 to 20 mM.

The therapeutic agent of the present invention may contain other low-molecular-weight polypeptides, proteins (e.g., serum albumin, gelatin, and immunoglobulin), amino acids, saccharides (e.g., polysaccharides and monosaccharides), carbohydrates, and sugar alcohols.

In the present invention, examples of the amino acid can include basic amino acids, for example, arginine, lysine, histidine, and ornithine, and inorganic salts of these amino acids (preferably, the form of hydrochloride or phosphate, i.e., amino acid phosphate). In the case of using a free amino acid, a preferred pH value is adjusted by the addition of an appropriate physiologically acceptable buffering substance, for example, an inorganic acid, particularly, hydrochloric acid, phosphoric acid, sulfuric acid, acetic acid, or formic acid, or a salt thereof. In this case, use of phosphate is particularly advantageous because a particularly stable freeze-dried product is obtained. This is particularly advantageous when the preparation is substantially free from an organic acid, for example, malic acid, tartaric acid, citric acid, succinic acid, or fumaric acid or when the corresponding anion (malic acid ion, tartaric acid ion, citric acid ion, succinic acid ion, or fumaric acid ion, etc.) is absent. The amino acid is preferably arginine, lysine, histidine, or ornithine. Alternatively, an acidic amino acid, for example, glutamic acid or aspartic acid or the form of a salt (preferably sodium salt) thereof, a neutral amino acid, for example, isoleucine, leucine, glycine, serine, threonine, valine, methionine, cysteine, or alanine, or an aromatic amino acid, for example, phenylalanine, tyrosine, tryptophan, or a derivative N-acetyltryptophan, may be used.

In the present invention, examples of the saccharide (e.g., polysaccharides and monosaccharides) or the carbohydrate can include dextran, glucose, fructose, lactose, xylose, mannose, maltose, sucrose, trehalose, and raffinose.

In the present invention, examples of the sugar alcohol can include mannitol, sorbitol, and inositol.

In the case of preparing an aqueous solution for injection from the drug of the present invention, the drug can be mixed with, for example, an isotonic solution containing saline, glucose, or other aids (e.g., D-sorbitol, D-mannose, D-mannitol, and sodium chloride). The aqueous solution may be further used in combination with an appropriate solubilizer (e.g., alcohols (ethanol, etc.), polyalcohols (propylene glycol, PEG, etc.), and nonionic surfactants (polysorbate 80 or HCO-50)).

The drug of the present invention may further contain, if desired, a diluent, a solubilizer, a pH adjuster, a soothing agent, a sulfur-containing reducing agent, an antioxidant, and the like.

In the present invention, examples of the sulfur-containing reducing agent can include those having a sulfhydryl group, such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acids having 1 to 7 carbon atoms.

In the present invention, examples of the antioxidant can include erythorbic acid, dibutylhydroxytoluene, butylhydroxyanisole, α-tocopherol, tocopherol acetate, L-ascorbic acid and salts thereof, L-ascorbic acid palmitate, L-ascorbic acid stearate, sodium bisulfite, sodium sulfite, triamyl gallate, propyl gallate, and chelating agents such as disodium ethylenediaminetetraacetate (EDTA), sodium pyrophosphate, and sodium metaphosphate.

If necessary, the IL-6 inhibitor may be enclosed in a microcapsule (microcapsule made of hydroxymethylcellulose, gelatin, poly[methyl methacrylate], or the like) or prepared into a colloid drug delivery system (liposomes, albumin microspheres, microemulsions, nanoparticles, and nanocapsules, etc.) (see e.g., "Remington's Pharmaceutical Science $16^{th}$ edition" Oslo Ed., 1980). Methods for formulating drugs as sustained-release drugs are also known in the art and may be applied to the present invention (Langer et al., J. Biomed. Mater. Res. 1981, 15: 167-277; Langer, Chem. Tech. 1982, 12: 98-105; U.S. Pat. No. 3,773,919; European Patent Publication No. EP 58,481; Sidman et al., Biopolymers 1983, 22: 547-556; and EP 133,988).

The pharmaceutically acceptable carrier used is selected appropriately or in combination from those described above according to a dosage form, though the pharmaceutically acceptable carrier is not limited thereto.

The present invention relates to a method for treating or and/or preventing mental illness in a subject, comprising the step of administering an IL-6 inhibitor such as an IL-6 receptor inhibitor to the subject having mental illness or the subject having the potential to develop mental illness.

In the present invention, the "subject" refers to a recipient organism of the therapeutic agent for mental illness of the present invention, or a portion within the body of the organism. The organism includes, but is not particularly limited to, animals (e.g., humans, livestock animal species, and wild animals).

In the present invention, the term "administer" includes oral or parenteral administration. Examples of the oral administration can include administration in the form of an oral agent. The oral agent can be selected from dosage forms such as granules, powders, tablets, capsules, solutions, emulsions, and suspensions.

Examples of the parenteral administration can include administration in the form of an injection. Examples of the injection can include subcutaneous injections, intramuscular injections, intravenous injections, and intraperitoneal injections. The drug of the present invention can also be locally administered to a region to be treated. For example, the administration can be achieved by local injection during operation or use of a catheter.

All prior art literatures cited herein are incorporated herein by reference.

The present invention will be described further specifically with reference to Examples. However, the present invention is not intended to be limited by these Examples. Those skilled in the art can make various changes or modifications. These changes and modifications are also included in the present invention.

EXAMPLES

Methods
Measurement of Startle Intensity

The measurement was performed by a modification of the method of Geyer et al. (Braff D L and Geyer M A, Arch Gen Psychiatry 1990, 47: 181-188). An acoustic startle response measurement apparatus for mice (O'HARA & CO., LTD.) was used in the startle response test. Each mouse was placed in a clear acrylic tube, which was then mounted in the apparatus. 65-dB background noise was generated, and the mouse was acclimatized thereto for 3 minutes. Then, the acoustic startle response was measured under conditions of 120-dB/40 ms of pulse sound with or without 78-dB to 90-dB/20 ms of prepulse sound. Specifically, the acoustic startle response was measured for each individual under conditions of the following sessions 1 to 35.
Sessions 1 to 5: 120-dB×5 rounds, continuous;
Sessions 6 to 30: 5 rounds each of five types of sessions (1) no prepulse+120-dB pulse, (2) 78-dB prepulse+120-dB pulse, (3) 84-dB prepulse+120-dB pulse, (4) 90-dB prepulse+120-dB pulse, and (5) no pulse (background), set so as to be randomly generated at any interval of 15 to 20 seconds; and
Sessions 31 to 35: 120-dB×5 rounds, continuous.

The average value (background) of the sessions (5) of sessions 6 to 30 was subtracted from the respective average startle intensities of the sessions (1) to (4) of sessions 6 to 30, and this value was used as the level of startle. The % rate of prepulse inhibition was calculated according to the following expression:

% rate of prepulse inhibition=100×(Level of startle at 120-dB—Level of startle in the presence of each prepulse)/Level of startle at 120-dB Measurement of IL-6 Concentration in Blood BD™ CBA Mouse Enhanced Sensitivity Flex set (cat #558301) was used as an IL-6 measurement reagent. Also, Mouse/Rat Soluble protein Master Buffer Kit (cat #558266) was used in reagent preparation. FACSCanto II (BD) was used in measurement and detection, and the concentration was calculated using FCAP Array™Software. The measurement was performed by a modification of the method with reference to the instruction manual issued by BD, as shown below.

Mouse plasma recovery: A mouse was euthanized by cervical dislocation. Then, the neck was immediately cut with surgical scissors, and blood was recovered into a 1.5 mL tube containing 15 µL of 100 mM EDTA and immediately mixed by inverting the tube. The tube was left standing at room temperature for 30 minutes and then centrifuged at 7000 g×10 minutes (4° C.) in a centrifuge, and the plasma portion of the supernatant was recovered into a fresh tube. The plasma was dispensed into 50 µL and stored in a deep freezer of −80° C. until measurement.

Standard preparation for calibration curve: A standard for IL-6 calibration curve included in the set described above was transferred from the vial to a 15 mL tube and thawed at room temperature by the addition of 4 mL of Assay Diluent (reagent included in Master Buffer Kit) (stock solution: 2500 pg/mL). 460 µL of Assay Diluent was placed in a 1.5 mL tube, and 40 µL of the IL-6 standard stock solution was added thereto for dilution to prepare a top standard (200 pg/ml). Then, 3-fold dilution was performed 7 times. 50 µL each of the diluted standards was placed in a fresh 1.5 mL tube and prepared for calibration curve.

Antibody reaction: The cryopreserved sample was thawed in ice. Beads for IL-6 measurement were diluted 10-fold with Capture Bead Diluent (reagent included in Master Buffer Kit). A 10 µL aliquot was added to the sample, the standard solution, or Assay Diluent (two blanks; with and without a secondary antibody), and the mixture was left standing at room temperature for 1 hour in the dark. Wash Buffer (250 µL/tube) was added to each tube, which was then centrifuged (500 g×10 min, 4° C.) for precipitation, followed by the removal of the supernatant. Capture beads were diluted 10-fold with Capture Bead Diluent (reagent included in Master Buffer Kit). A 10 µL aliquot was added to the sample, the standard solution, or one of the blank controls (with a secondary antibody), and the mixture was left standing at room temperature for 1 hour in the dark. 10 µL of Capture Bead Diluent was added to the other blank control (without a secondary antibody). Wash Buffer (250 µL/tube) was added to each tube, which was then centrifuged (500 g×10 min, 4° C.) for precipitation, followed by the removal of the supernatant. The precipitates were suspended in 150 µL of Wash Buffer. Then, the suspension was transferred to a 5 mL polystyrene round tube for FACS measurement (unsterilized). The measurement was performed using BD FACSDiva™ software in FACSCanto II. The bead population was gated in a dot plot of SSC-A on the ordinate against FSC-A on the abscissa. The bead location (B4) of IL-6 was gated in a dot plot of APC-Cy7-A on the ordinate against APC-A on the abscissa. Another dot plot of APC-Cy7-A on the ordinate against PE-A on the abscissa was prepared. The beads were taken up while PE intensity was confirmed to shift to the right in a concentration-dependent manner for the IL-6 standard. The concentration was calculated using FCAP Array™ Software.

Reference Example 1: High Fat Diet Feeding Experiment on Male C57B6/J Mouse-1

In order to minimize an error of a behavior test, 5-week-old male C57B6/J mice were prepared by the following method: male and female mice for mating were purchased from Charles River Laboratories Japan, Inc. and bred in Small Animal Research Facility of National Institute of Neuroscience, NCNP. After birth, only male offspring was kept in delivery cages. The mice that became 3 weeks old were weaned, divided into 3 to 4 individuals per cage, and raised until 5 weeks old.

The 5-week-old male C57B6/J mice were allowed to freely eat a normal diet CE-2 (CLEA Japan, Inc.) or a high fat diet High Fat Diet 32 (CLEA Japan, Inc.) for 5 weeks (from the ages of 5 weeks to 10 weeks) or 10 weeks (from the ages of 5 weeks to 15 weeks) (FIG. 1).

The mice fed with the normal diet or the high fat diet for 10 weeks were examined for prepulse inhibition in acoustic startle response. The startle response was measured for each individual of the normal diet group (ND; n=20) and the high fat diet group (HFD; n=28) in the presence and absence of prepulse (78, 84, or 90 dB). Mean±standard deviation of each group was calculated on the basis of the % rate of prepulse inhibition of each individual.

Figure 3:
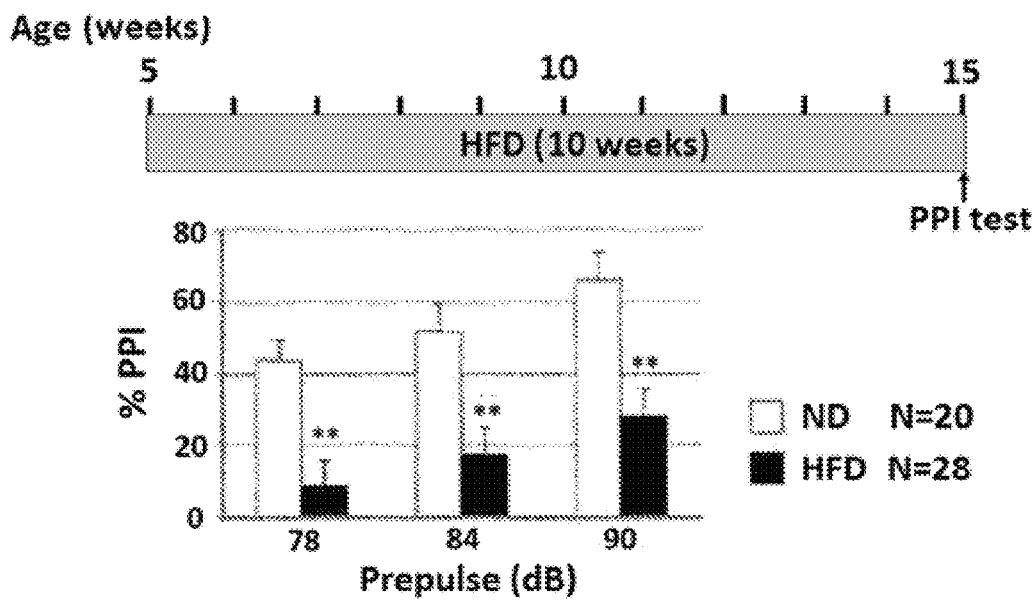
FIG. 3 is a diagram showing that PPI deterioration can be induced by feeding 5-week-old mice with a high fat diet for 10 weeks.

The results are shown in FIG. 3. The prepulse inhibition was remarkably deteriorated (attenuated) in the high fat diet group as compared with the normal diet group. Thus, it was found that the deterioration of prepulse inhibition can be induced by feeding 5-week-old mice with a high fat diet for 10 weeks.

Figure 4:
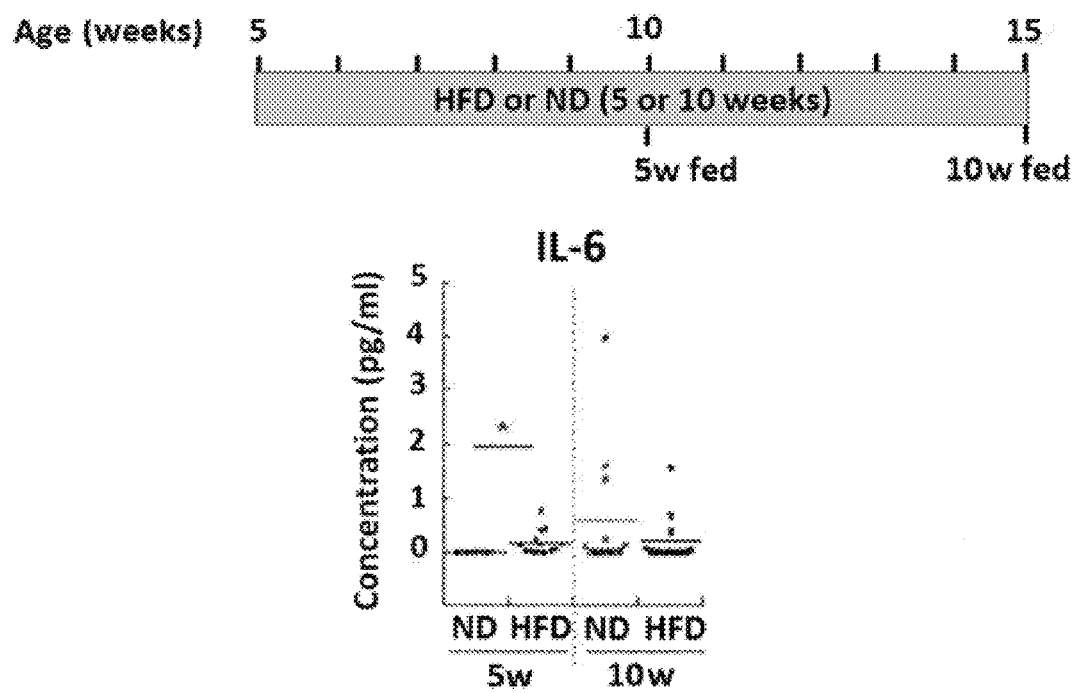
FIG. 4 is a diagram showing the influence of high fat feeding on IL-6 concentrations in blood.

The IL-6 concentration in blood was further measured for the mice fed with the normal diet or the high fat diet for 5 weeks or 10 weeks (FIG. 4). In the case of the 5-week feeding, the IL-6 concentration in blood was significantly increased in the high fat diet group as compared with the normal diet group. On the other hand, in the case of the 10-week feeding, no significant difference in IL-6 concentration in blood was confirmed between the high fat diet group and the normal diet group.

These results suggest the possibility that: IL-6 plays an important role in the deterioration of prepulse inhibition at the initial stage of induction of schizophrenia-like abnormal behavior; and a molecule secondarily induced by IL-6 is involved in the deterioration of prepulse inhibition. The possible reasons why no difference in IL-6 concentration was confirmed between the high fat diet feeding group and the normal diet feeding group after 10 weeks are that: a rise in IL-6 concentration is found even in the normal diet feeding group due to aging; and some change in signaling substance or the like in the brain is induced more complicatedly in 10 weeks of high fat diet feeding than at the initial stage.

Reference Example 2: High Fat Diet Feeding Experiment on Male C57B6/J Mouse-2

In the case of performing antibody administration mentioned later in the experiment system of high fat diet feeding for 10 weeks from the age of 5 weeks, the number of antibody doses is a total of 10 (1/week) per individual, and the amount of the antibody used is large. Accordingly, in order to establish a system capable of determining the effect of MR16-1 with a fewer number of doses, conditions for inducing the deterioration of prepulse inhibition in a shorter period were studied.

Eight-week-old male C57B6/J mice were allowed to freely eat a normal diet CE-2 or a high fat diet High Fat Diet 32 for 3 weeks (from the ages of 8 weeks to 11 weeks). At the age of 11 weeks, each mouse of the normal diet group (ND; n=20) and the high fat diet group (HFD; n=28) was examined for prepulse inhibition in acoustic startle response in the same way as in Reference Example 1.

Figure 5:
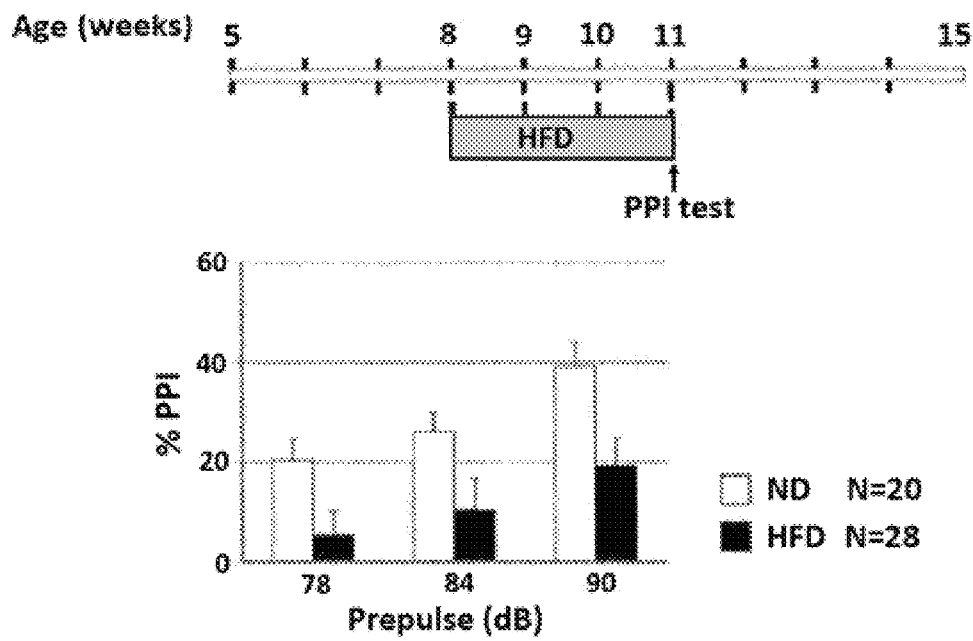
FIG. 5 is a diagram showing that PPI deterioration can be induced by feeding 8-week-old mice with a high fat diet for 3 weeks.
Figure 6:
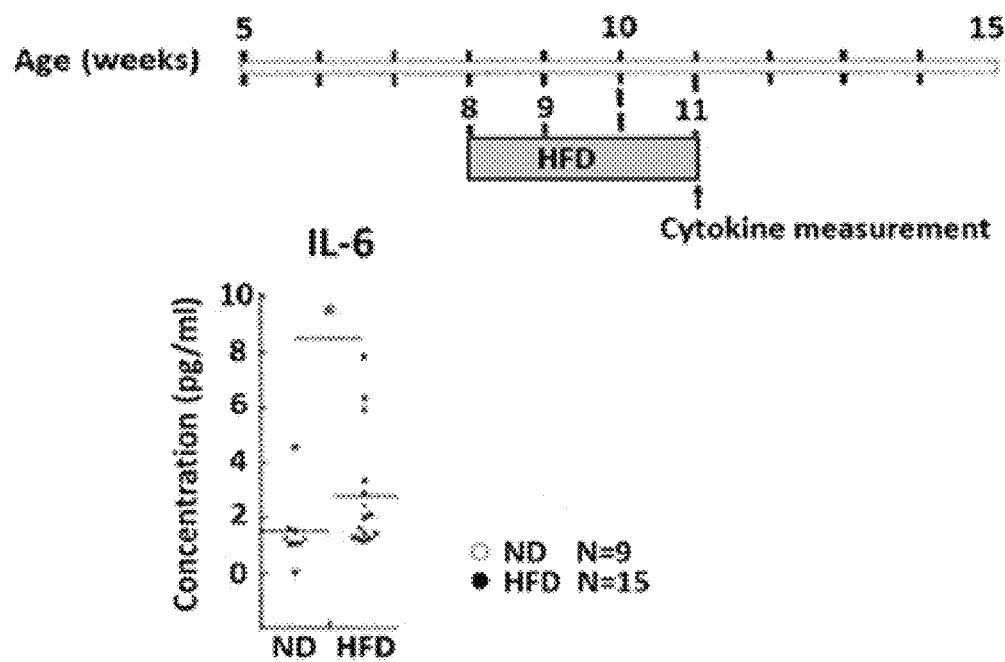
FIG. 6 is a diagram showing that IL-6 concentrations in blood are increased by feeding 8-week-old mice with a high fat diet for 3 weeks.

The results are shown in FIG. 5. The prepulse inhibition was deteriorated in the high fat diet group as compared with the normal diet group. Thus, it was found that the deterioration of prepulse inhibition can also be induced by feeding 8-week-old mice with a high fat diet for 3 weeks. Also, significant increase in IL-6 concentration in blood was confirmed in the high fat diet feeding for 3 weeks from the age of 8 weeks, as compared with the normal diet-fed mice (FIG. 6).

Example 1: Effect of Anti-IL-6 Receptor Antibody on Prepulse Inhibition

Eight-week-old male C57B6/J mice were allowed to freely eat a normal diet CE-2 or a high fat diet High Fat Diet 32 for 3 weeks (from the ages of 8 weeks to 11 weeks). An anti-IL-6 receptor antibody MR16-1 (Chugai Pharmaceutical Co., Ltd.) or a vehicle was administered to the high fat diet group three times (once each at the ages of 8, 9, and 10 weeks) while a vehicle was administered to the normal diet group three times (once each at the ages of 8, 9, and 10 weeks). The MR16-1 was administered by intraperitoneal injection at doses of 1 mg/mouse at the age of 8 weeks, 0.5 mg/mouse at the age of 9 weeks, and 0.5 mg/mouse at the age of 10 weeks. At the age of 11 weeks, each mouse was examined for prepulse inhibition in acoustic startle response in the same way as in Reference Example 1.

Figure 7:
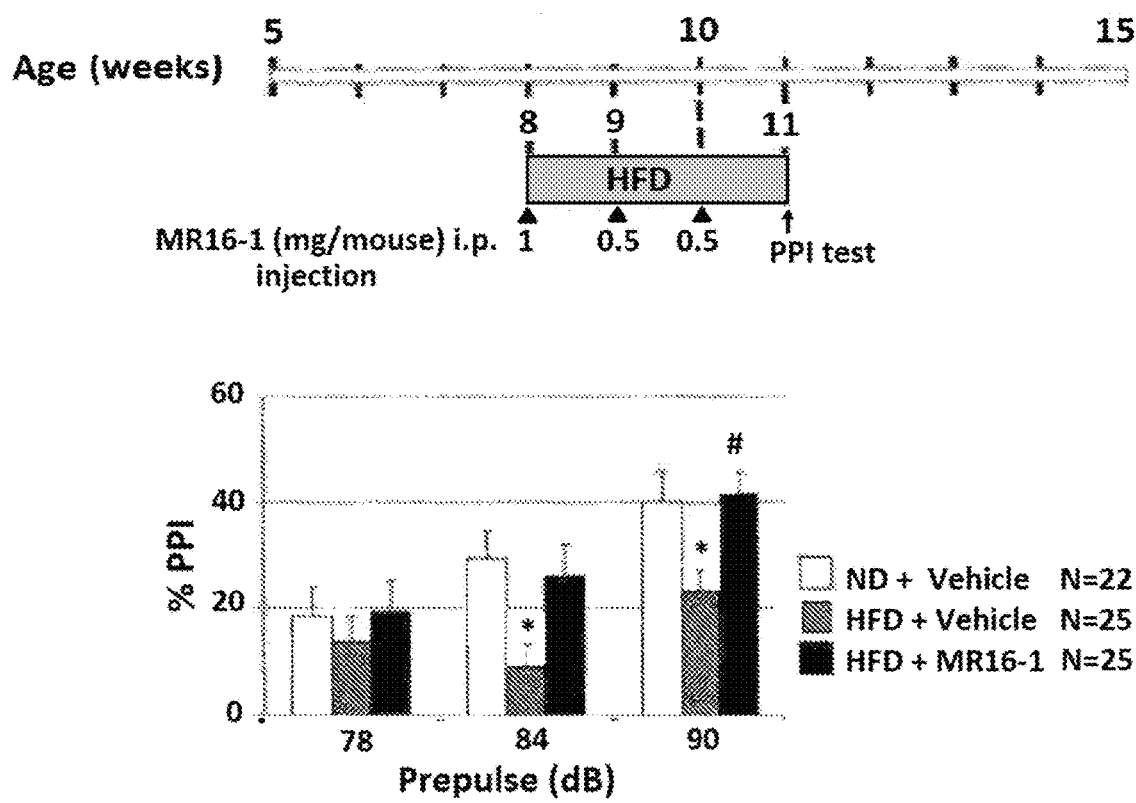
FIG. 7 is a diagram showing that PPI deterioration caused by high fat diet feeding is suppressed by the administration of an anti-IL-6 receptor antibody MR16-1.

The results are shown in FIG. 7. The prepulse inhibition was deteriorated in the high fat diet group given the vehicle (HFD+Vehicle; n=25) as compared with the normal diet group (ND+Vehicle; n=22). Particularly, the prepulse inhibition was remarkably deteriorated when the prepulse was 84 dB or 90 dB. On the other hand, the prepulse inhibition was confirmed in the high fat diet group given MR16-1 (HFD+MR16-1; n=25) at the same level with the normal diet group. Thus, it was found that the deterioration of prepulse inhibition by high fat diet feeding is suppressed by the administration of an anti-IL-6 receptor antibody.

Example 2: Influence of Anti-IL-6 Receptor Antibody on Phosphorylation and Protein Expression Level of GSK3a/a in Striatum and Prefrontal Cortex It is known that change in the phosphorylation or expression level of GSK3α/β is found in the brain after death of a schizophrenia patient. Accordingly, in order to reveal the mechanism of action of an anti-IL-6 receptor antibody on the deterioration of prepulse inhibition induced in the high fat diet-fed mice described above, its influence on the phosphorylation and protein expression level of GSK3a/a in the striatum and the prefrontal cortex was analyzed.
Experiment Method Eight-week-old male C57B6/J mice were allowed to freely eat a normal diet CE-2 or a high fat diet High Fat Diet 32 for 3 weeks (from the ages of 8 weeks to 11 weeks). An anti-IL-6 receptor antibody MR16-1 (Chugai Pharmaceutical Co., Ltd.) or a vehicle was administered to the high fat diet group three times (once each at the ages of 8, 9, and 10 weeks) while a vehicle was administered to the normal diet group three times (once each at the ages of 8, 9, and 10 weeks). The MR16-1 was administered by intraperitoneal injection at doses of 1 mg/mouse at the age of 8 weeks, 0.5 mg/mouse at the age of 9 weeks, and 0.5 mg/mouse at the age of 10 weeks. At the age of 11 weeks, the brain was immediately excised from each mouse after cervical dislocation and placed in cooled PBS. After 10 seconds, the brain was loaded in a brain slicer for mice (EM Japan) and cut into a thickness of 1 mm using a razor. The slices were immediately transferred into a tray containing cooled PBS. According to the brain atlas prepared by Van De Werd et al. (Van De Werd H J and Uylings H B, Brain Struct Funct, 2014, 219: 433-459), the striatum site from the bregma +0.74 section and the prefrontal cortex site from the bregma +1.70 section were each recovered into a 1.5 mL tube using a biopsy punch having a diameter of 1.5 mm (Kai Corp.), placed in liquid nitrogen, and immediately cryopreserved. For the analysis method of Western blot, sample treatment and Western blot were performed with reference to the report of Numakawa et al. (Numakawa T et al., Proc Natl Acad Sci USA, 2009, 106: 647-652). The primary antibodies used were an anti-phosphorylated GSK3α/β antibody (1:2000; rabbit polyclonal, #9331, Cell Signaling Technology, Japan), an anti-GSK3α/β antibody (1:2000; mouse monoclonal (0011-A), sc-7291, Santa Cruz Biotechnology Inc., CA, USA), and an anti-β-actin antibody (1:5000; mouse monoclonal, A-5441, Sigma Aldrich, MO, USA). The secondary antibodies used were a peroxidase-conjugated anti-mouse IgG antibody (1:1000; goat polyclonal, Jackson Immunology Research Laboratories Inc., PA, USA) and an anti-rabbit IgG antibody (1:1000; goat polyclonal, Rockland Immunochemicals, Inc., PA, USA). ImmunoStar (R) (Wako Pure Chemical Industries, Ltd., Tokyo, Japan) was used in the detection of Immunoblotting bands. Immunoreactivity was analyzed using CS Analyzer software 3 (ATTO & Rise Corp., Tokyo, Japan). β-actin was used in normalization.

Results

Figure 8A:
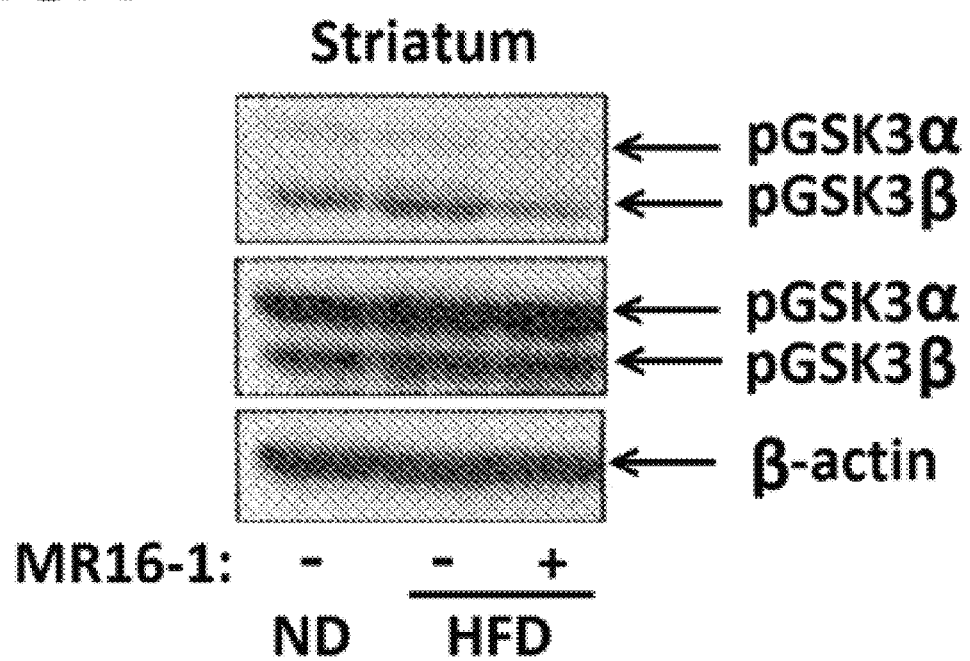
FIGS. 8A-8E are diagrams showing the influence of an anti-IL-6 receptor antibody on the phosphorylation and protein expression level of GSK3α/β in the striatum. **p<0.01.
Figure 8B:
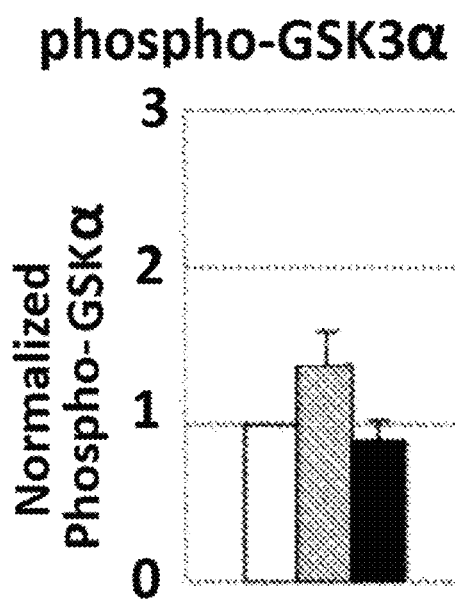
Figure 8C:
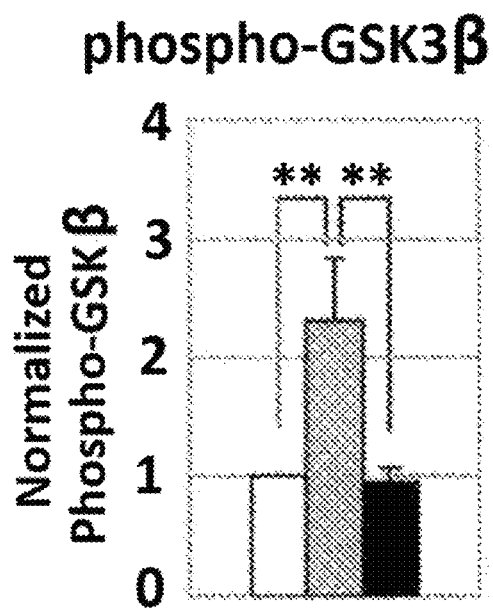
Figure 8D:
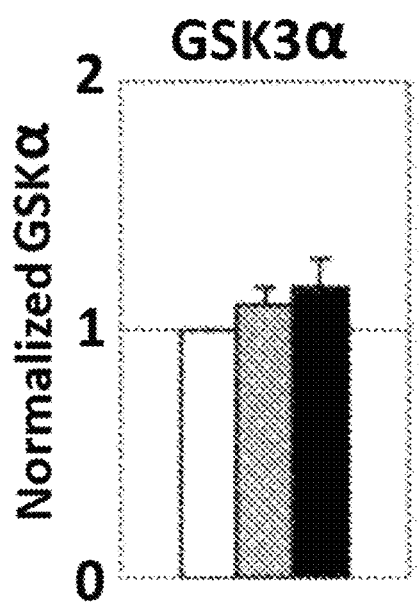
Figure 8E:
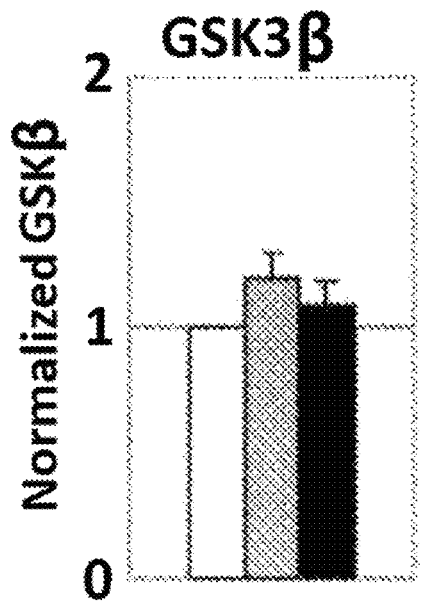
Figure 9A:
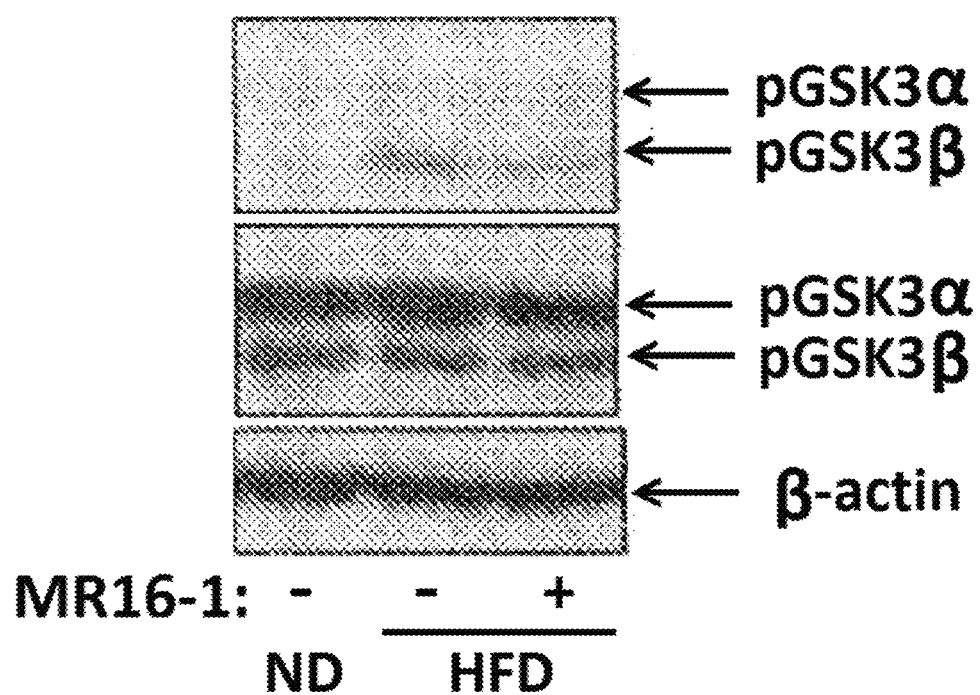
FIGS. 9A-9E are diagrams showing the influence of an anti-IL-6 receptor antibody on the phosphorylation and protein expression level of GSK3α/β in the prefrontal cortex.
Figure 9B:
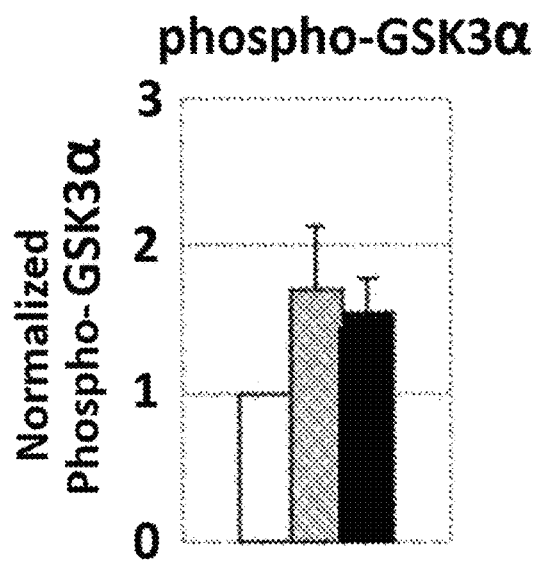
Figure 9C:
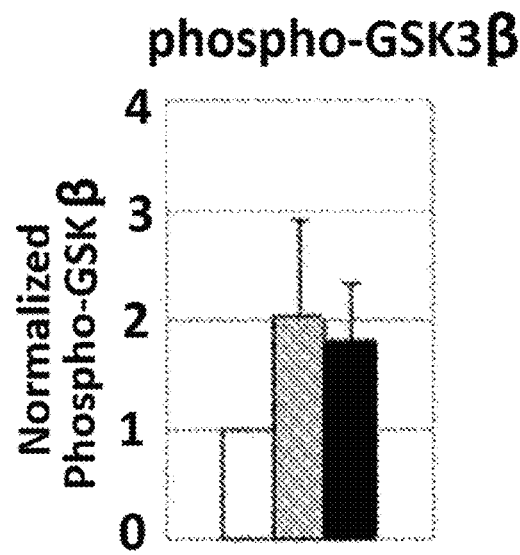
Figure 9D:
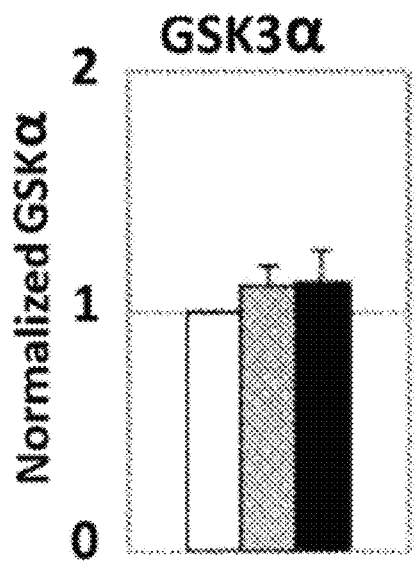
Figure 9E:
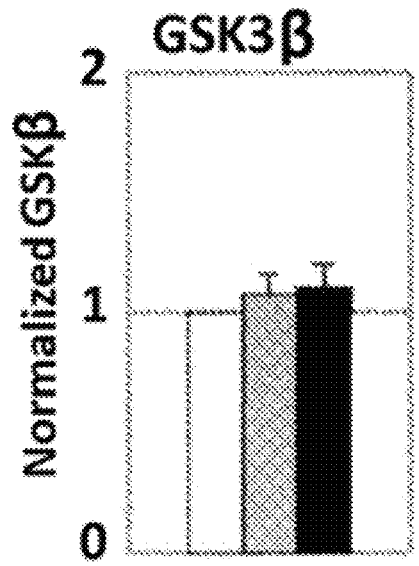

GSK3β in the striatum was hyperphosphorylated in the high fat diet-fed mice. The obtained results indicate that the hyperphosphorylation of GSK3β is inhibited by the administration of MR16-1 (FIGS. 8A and 8C). No difference in the phosphorylation of GSK3α and the protein expression level of GSK3α/β in the striatum was found between the presence and absence of high fat diet feeding and the presence and absence of MR16-1 administration (FIGS. 8A-8E). Also, no significant difference in the phosphorylation and protein expression level of GSK3α/β in the prefrontal cortex was found between the presence and absence of high fat diet feeding and the presence and absence of MR16-1 administration (FIGS. 9A-9E). These results suggested the possibility that MR16-1 prevents the induction of prepulse inhibition deterioration by specifically inhibiting the hyperphosphorylation of GSK3β in the striatum.

INDUSTRIAL APPLICABILITY

The present invention provides a novel therapeutic agent for mental illness that differs totally in the mechanism of action from conventional drugs for treating mental illness.

The invention claimed is:

1. A method for treating schizophrenia in a subject, the method comprising the steps of:
   (a) measuring startle response in a subject by using a startle response test,
   (b) determining the subject has schizophrenia and attenuation of prepulse inhibition of startle, and
   (c) administering an effective amount of an interleukin 6 (IL-6) inhibitor to the subject;
   wherein the IL-6 inhibitor is an IL-6 antibody or an IL-6 receptor antibody; and
   wherein the method suppresses the attenuation of prepulse inhibition of startle in the subject, as determined using a startle response test.

2. The method according to claim 1, wherein the IL-6 inhibitor is an anti-IL-6 receptor antibody.

3. The method according to claim 2, wherein the anti-IL-6 receptor antibody is a chimeric antibody, a humanized antibody, or a human antibody.

4. A method for treating schizophrenia in a subject, the method comprising the step of:
   (a) measuring startle response in a subject by using a startle response test,
   (b) determining the subject has schizophrenia and attenuation of prepulse inhibition of startle, and
   (c) administering an effective amount of an interleukin 6 (IL-6) inhibitor to the subject;
   wherein the IL-6 inhibitor is an IL-6 receptor antibody and wherein the anti-IL-6 receptor antibody is humanized PM-1 antibody; and
   wherein the method suppresses the attenuation of prepulse inhibition of startle in the subject, as determined using a startle response test.

* * * * *